US011490971B2

(12) United States Patent
Betsugi et al.

(10) Patent No.: US 11,490,971 B2
(45) Date of Patent: Nov. 8, 2022

(54) DRIVER INTERFACE, ROBOTIC SURGICAL APPARATUS, AND METHOD OF DETECTING ATTACHMENT OF SURGICAL INSTRUMENT TO DRIVER INTERFACE

(71) Applicant: MEDICAROID CORPORATION, Kobe (JP)

(72) Inventors: Shota Betsugi, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 362 days.

(21) Appl. No.: 16/537,350

(22) Filed: Aug. 9, 2019

(65) Prior Publication Data

US 2020/0069379 A1   Mar. 5, 2020

(30) Foreign Application Priority Data

Aug. 28, 2018 (JP) .............................. JP2018-159334
Mar. 28, 2019 (JP) .............................. JP2019-063408

(51) Int. Cl.
*A61B 34/30* (2016.01)
*A61B 34/00* (2016.01)

(52) U.S. Cl.
CPC .............. *A61B 34/30* (2016.02); *A61B 34/25* (2016.02); *A61B 34/70* (2016.02); *A61B 2034/302* (2016.02)

(58) Field of Classification Search
CPC ......... A61B 34/30; A61B 34/25; A61B 34/70; A61B 2034/302; A61B 34/71; A61B 46/10; A61B 2090/0808; A61B 17/00234; A61B 34/37; A61B 2017/00477; A61B 90/06; A61B 1/00133; A61B 1/0016; A61B 2090/0806; A61B 2090/0811; A61B 17/29; A61M 25/0105
See application file for complete search history.

(56) References Cited

U.S. PATENT DOCUMENTS

| 5,413,573 | A | 5/1995 | Koivukangas |
|---|---|---|---|
| 8,142,447 | B2 | 3/2012 | Cooper et al. |
| 9,724,163 | B2 | 8/2017 | Orban |
| 10,045,828 | B2 | 8/2018 | Dachs, II et al. |

(Continued)

FOREIGN PATENT DOCUMENTS

| CN | 106102631 A | 11/2016 |
|---|---|---|
| CN | 106132344 A | 11/2016 |

(Continued)

*Primary Examiner* — Jocelin C Tanner
(74) *Attorney, Agent, or Firm* — Metrolex IP Law Group, PLLC

(57) ABSTRACT

A driver interface according to an embodiment may include an engagement member, an actuator, a detection member, and a sensor. The engagement member includes an engagement protrusion protruding from a surface of the engagement member and provided corresponding to an engagement recess provided at a drive transmission member rotatably provided in an adaptor. The actuator is configured to rotate the engagement member. The detection member is movable in a direction parallel to the rotation axis of the engagement member. The sensor detects the detection member that has moved as a result of contact with a part of the drive transmission member.

18 Claims, 20 Drawing Sheets

(56) References Cited

U.S. PATENT DOCUMENTS

| | | | |
|---|---|---|---|
| 2008/0046122 A1* | 2/2008 | Manzo | A61B 34/71 700/245 |
| 2013/0211397 A1* | 8/2013 | Parihar | A61B 34/30 606/130 |
| 2016/0361126 A1 | 12/2016 | Schena et al. | |
| 2016/0361127 A1 | 12/2016 | Dachs, II et al. | |
| 2016/0361131 A1 | 12/2016 | Dachs, II et al. | |
| 2017/0143438 A1 | 5/2017 | Komuro | |
| 2018/0228559 A1* | 8/2018 | Brierton | A61B 90/98 |
| 2019/0083189 A1 | 3/2019 | Wada | |

FOREIGN PATENT DOCUMENTS

| | | |
|---|---|---|
| CN | 107028660 A | 8/2017 |
| GB | 2552855 A | 2/2018 |
| JP | 2017-514544 A | 6/2017 |
| JP | 2017-514545 A | 6/2017 |
| WO | 2018/122979 A1 | 7/2018 |

\* cited by examiner

FIG. 9A
FIG. 9B
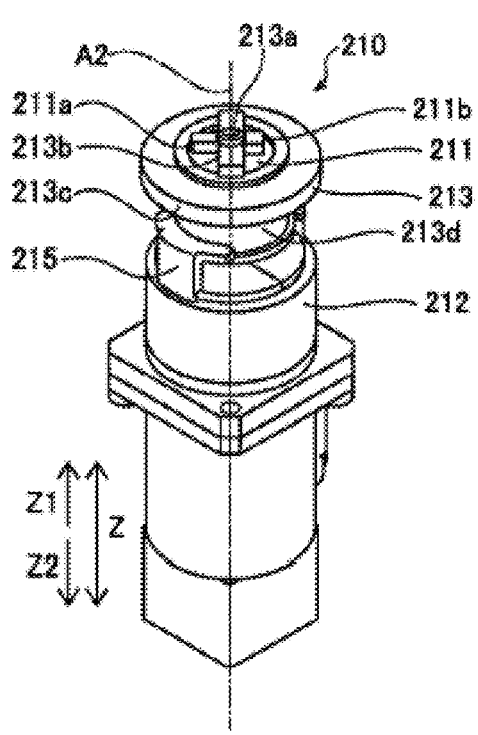
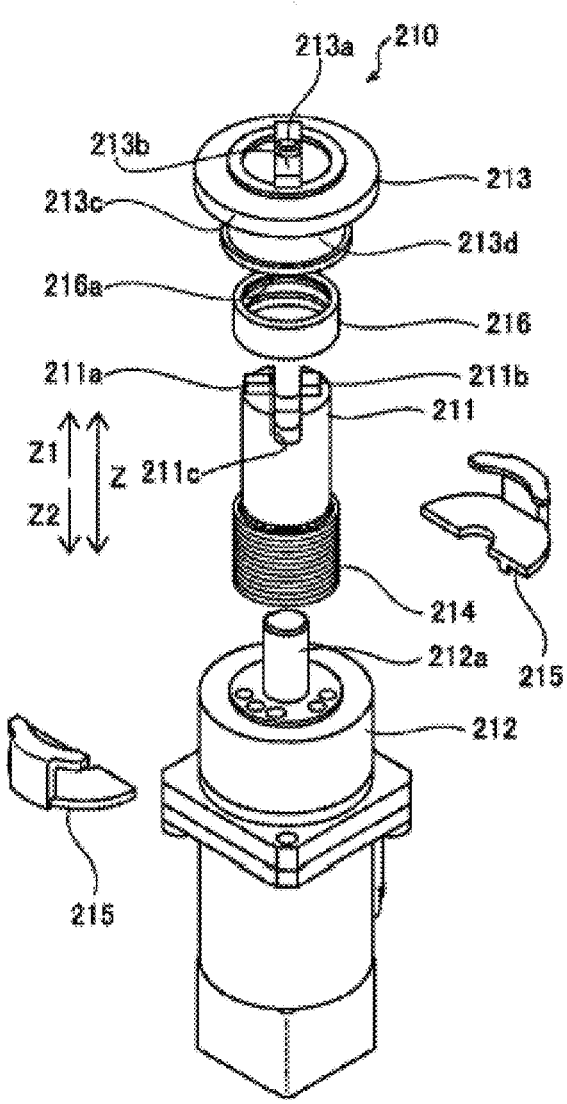

FIG. 11

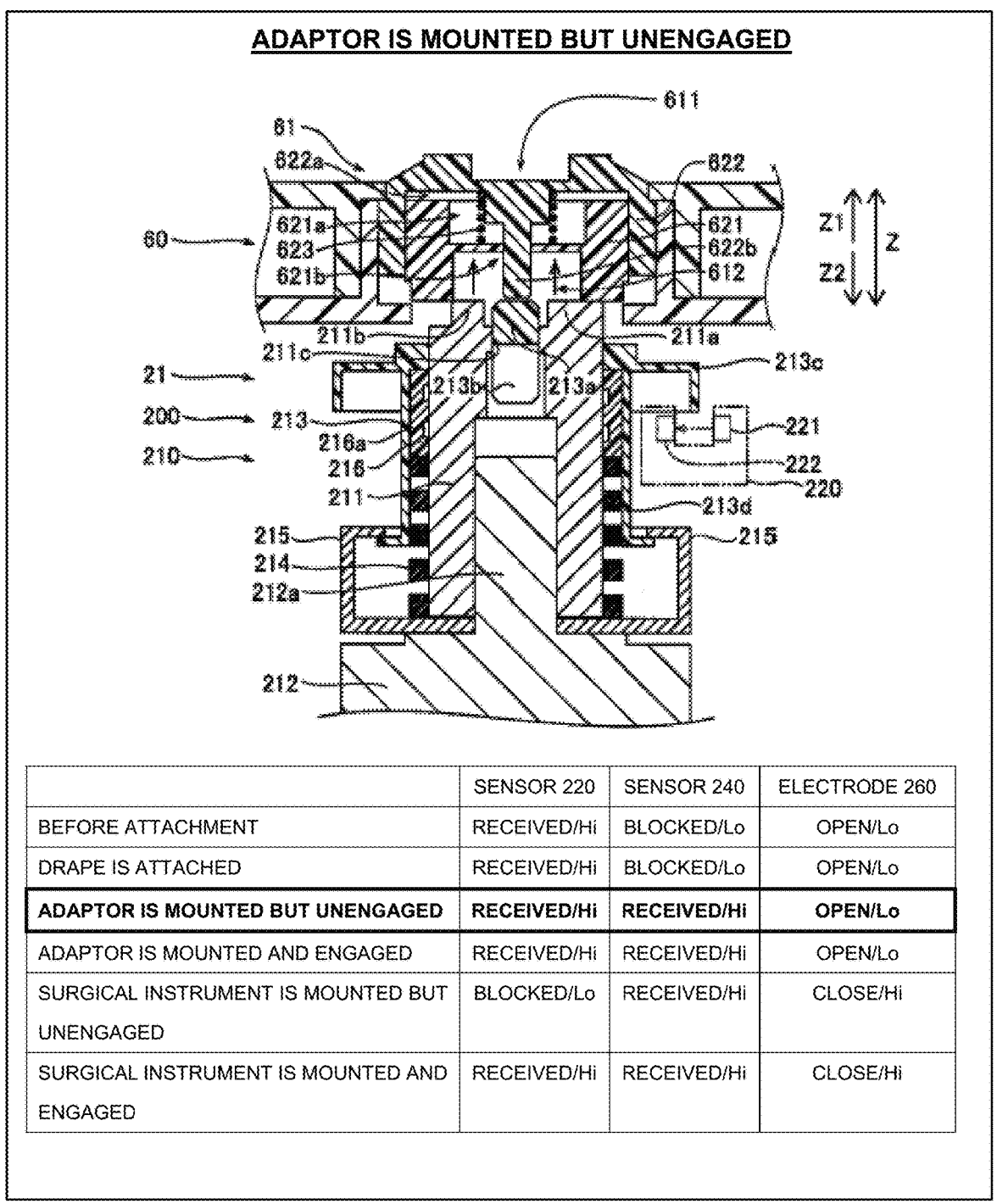

| | SENSOR 220 | SENSOR 240 | ELECTRODE 260 |
|---|---|---|---|
| BEFORE ATTACHMENT | RECEIVED/Hi | BLOCKED/Lo | OPEN/Lo |
| DRAPE IS ATTACHED | RECEIVED/Hi | BLOCKED/Lo | OPEN/Lo |
| ADAPTOR IS MOUNTED BUT UNENGAGED | RECEIVED/Hi | RECEIVED/Hi | OPEN/Lo |
| ADAPTOR IS MOUNTED AND ENGAGED | RECEIVED/Hi | RECEIVED/Hi | OPEN/Lo |
| SURGICAL INSTRUMENT IS MOUNTED BUT UNENGAGED | BLOCKED/Lo | RECEIVED/Hi | CLOSE/Hi |
| SURGICAL INSTRUMENT IS MOUNTED AND ENGAGED | RECEIVED/Hi | RECEIVED/Hi | CLOSE/Hi |

FIG. 12

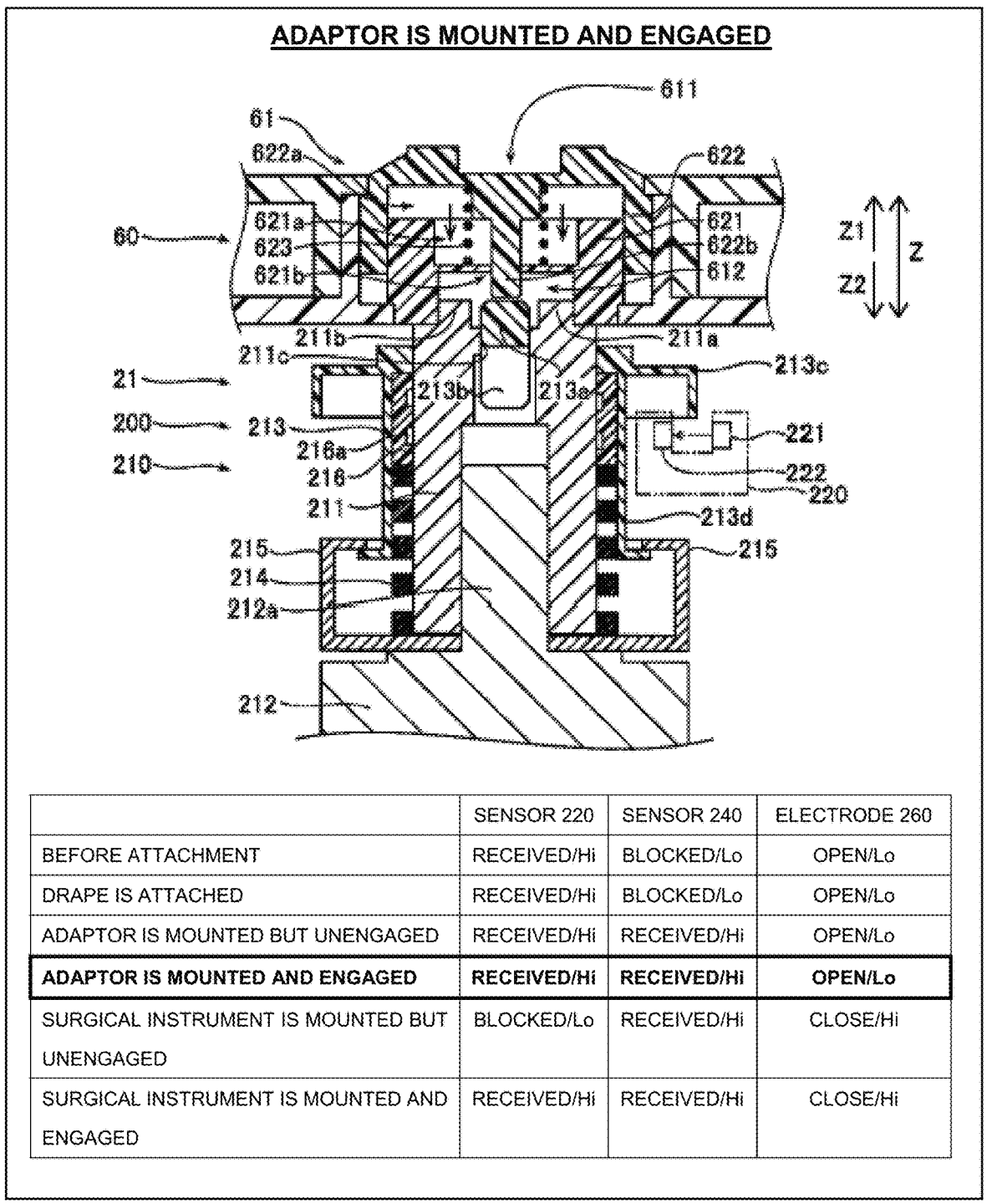

| | SENSOR 220 | SENSOR 240 | ELECTRODE 260 |
|---|---|---|---|
| BEFORE ATTACHMENT | RECEIVED/Hi | BLOCKED/Lo | OPEN/Lo |
| DRAPE IS ATTACHED | RECEIVED/Hi | BLOCKED/Lo | OPEN/Lo |
| ADAPTOR IS MOUNTED BUT UNENGAGED | RECEIVED/Hi | RECEIVED/Hi | OPEN/Lo |
| ADAPTOR IS MOUNTED AND ENGAGED | RECEIVED/Hi | RECEIVED/Hi | OPEN/Lo |
| SURGICAL INSTRUMENT IS MOUNTED BUT UNENGAGED | BLOCKED/Lo | RECEIVED/Hi | CLOSE/Hi |
| SURGICAL INSTRUMENT IS MOUNTED AND ENGAGED | RECEIVED/Hi | RECEIVED/Hi | CLOSE/Hi |

FIG. 13

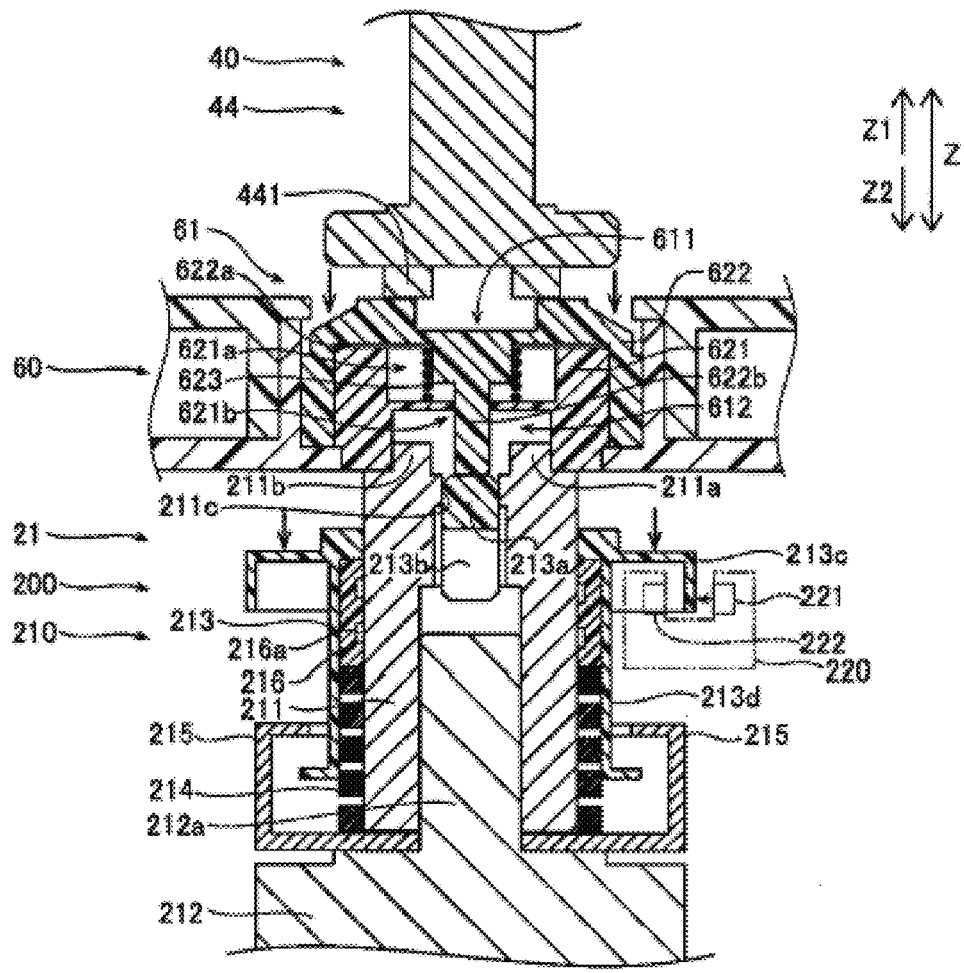

SURGICAL INSTRUMENT IS MOUNTED BUT UNENGAGED

|  | SENSOR 220 | SENSOR 240 | ELECTRODE 260 |
|---|---|---|---|
| BEFORE ATTACHMENT | RECEIVED/Hi | BLOCKED/Lo | OPEN/Lo |
| DRAPE IS ATTACHED | RECEIVED/Hi | BLOCKED/Lo | OPEN/Lo |
| ADAPTOR IS MOUNTED BUT UNENGAGED | RECEIVED/Hi | RECEIVED/Hi | OPEN/Lo |
| ADAPTOR IS MOUNTED AND ENGAGED | RECEIVED/Hi | RECEIVED/Hi | OPEN/Lo |
| SURGICAL INSTRUMENT IS MOUNTED BUT UNENGAGED | BLOCKED/Lo | RECEIVED/Hi | CLOSE/Hi |
| SURGICAL INSTRUMENT IS MOUNTED AND ENGAGED | RECEIVED/Hi | RECEIVED/Hi | CLOSE/Hi |

INTEGRATED STRUCTURE

SPLITED STRCUTRE

FIG. 21

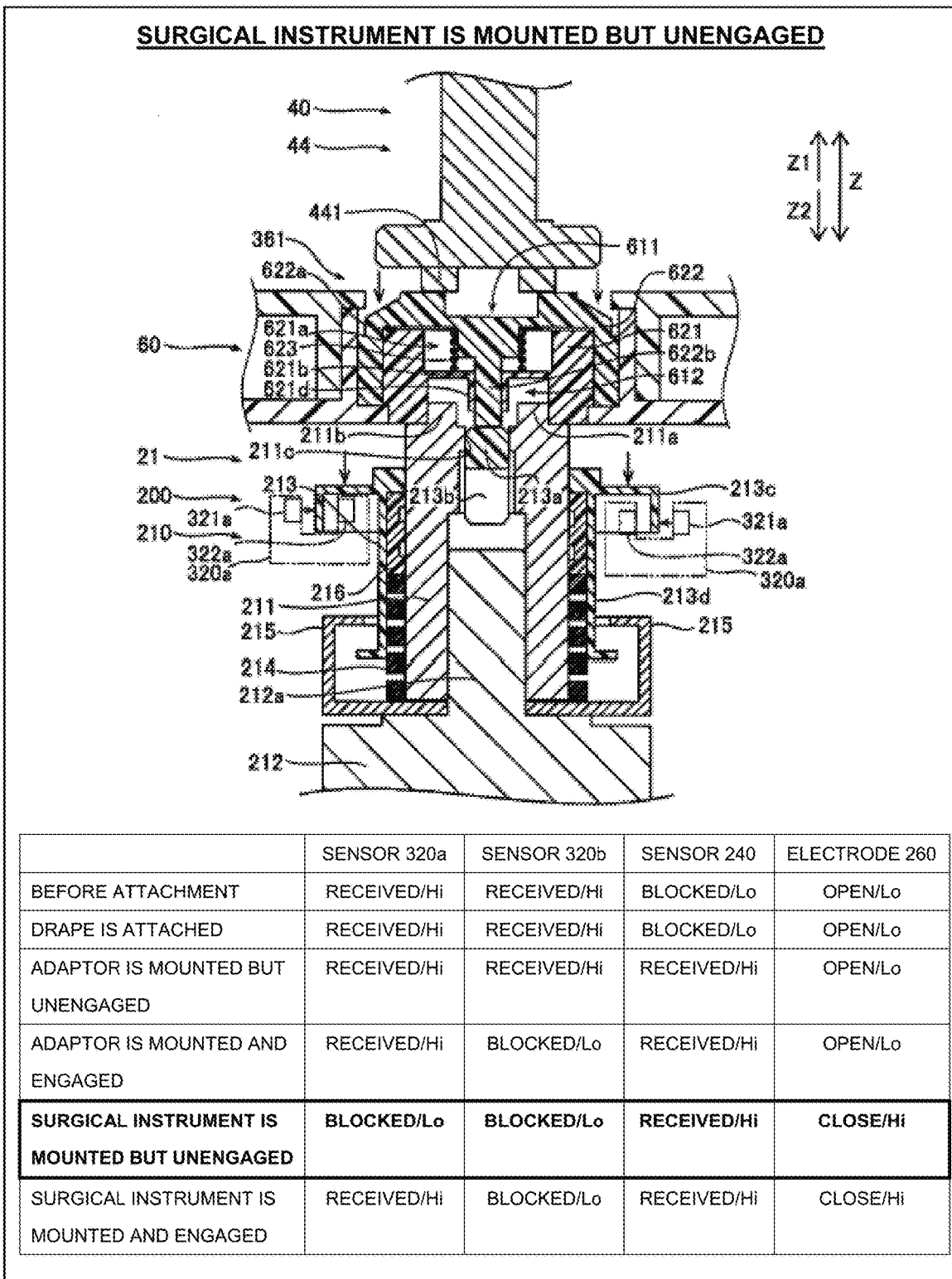

| | SENSOR 320a | SENSOR 320b | SENSOR 240 | ELECTRODE 260 |
|---|---|---|---|---|
| BEFORE ATTACHMENT | RECEIVED/Hi | RECEIVED/Hi | BLOCKED/Lo | OPEN/Lo |
| DRAPE IS ATTACHED | RECEIVED/Hi | RECEIVED/Hi | BLOCKED/Lo | OPEN/Lo |
| ADAPTOR IS MOUNTED BUT UNENGAGED | RECEIVED/Hi | RECEIVED/Hi | RECEIVED/Hi | OPEN/Lo |
| ADAPTOR IS MOUNTED AND ENGAGED | RECEIVED/Hi | BLOCKED/Lo | RECEIVED/Hi | OPEN/Lo |
| SURGICAL INSTRUMENT IS MOUNTED BUT UNENGAGED | BLOCKED/Lo | BLOCKED/Lo | RECEIVED/Hi | CLOSE/Hi |
| SURGICAL INSTRUMENT IS MOUNTED AND ENGAGED | RECEIVED/Hi | BLOCKED/Lo | RECEIVED/Hi | CLOSE/Hi |

FIG. 23

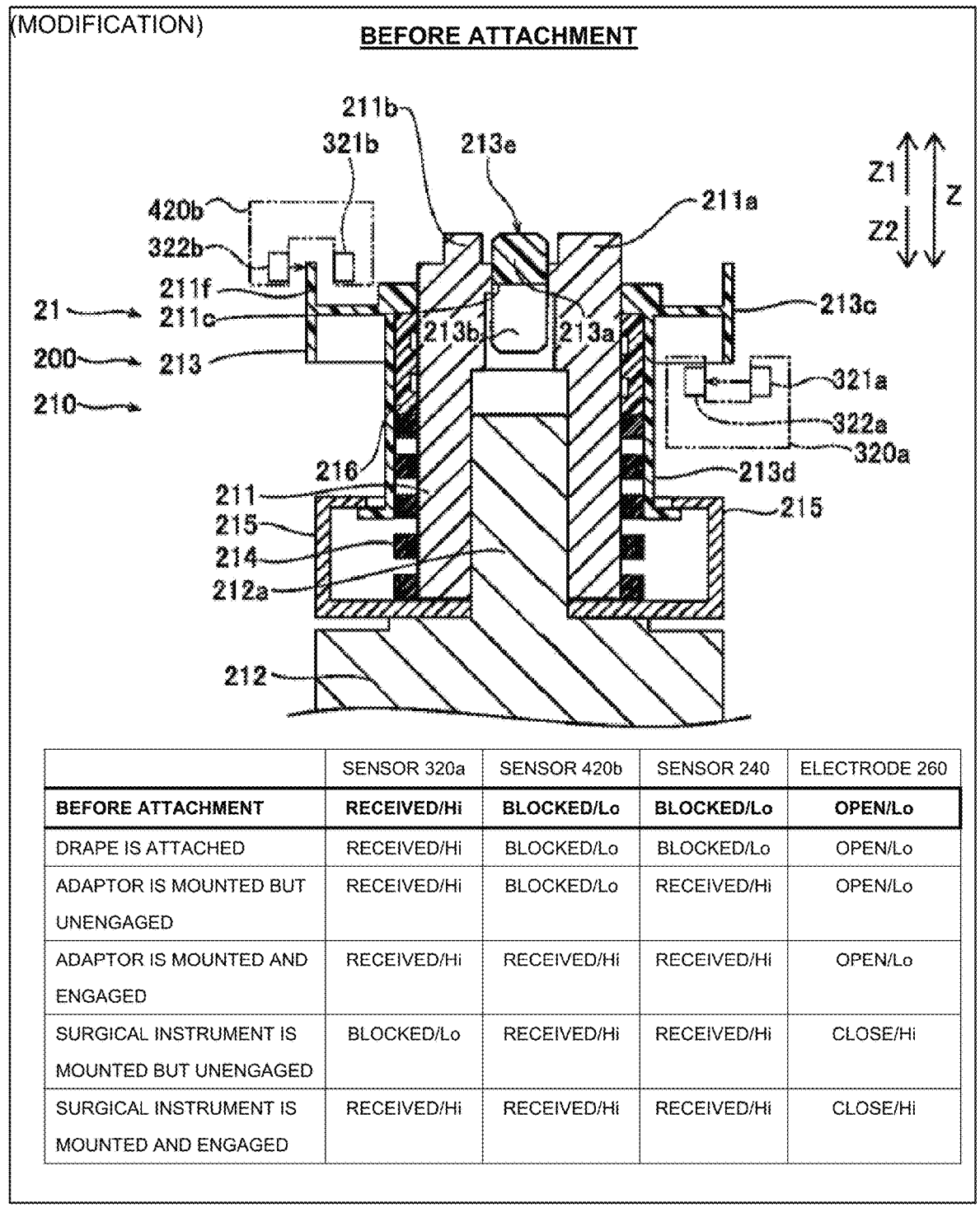

|  | SENSOR 320a | SENSOR 420b | SENSOR 240 | ELECTRODE 260 |
|---|---|---|---|---|
| BEFORE ATTACHMENT | RECEIVED/Hi | BLOCKED/Lo | BLOCKED/Lo | OPEN/Lo |
| DRAPE IS ATTACHED | RECEIVED/Hi | BLOCKED/Lo | BLOCKED/Lo | OPEN/Lo |
| ADAPTOR IS MOUNTED BUT UNENGAGED | RECEIVED/Hi | BLOCKED/Lo | RECEIVED/Hi | OPEN/Lo |
| ADAPTOR IS MOUNTED AND ENGAGED | RECEIVED/Hi | RECEIVED/Hi | RECEIVED/Hi | OPEN/Lo |
| SURGICAL INSTRUMENT IS MOUNTED BUT UNENGAGED | BLOCKED/Lo | RECEIVED/Hi | RECEIVED/Hi | CLOSE/Hi |
| SURGICAL INSTRUMENT IS MOUNTED AND ENGAGED | RECEIVED/Hi | RECEIVED/Hi | RECEIVED/Hi | CLOSE/Hi |

DRIVER INTERFACE, ROBOTIC SURGICAL APPARATUS, AND METHOD OF DETECTING ATTACHMENT OF SURGICAL INSTRUMENT TO DRIVER INTERFACE

CROSS REFERENCE TO RELATED APPLICATIONS

This application claims priority to Japanese Patent Application No. 2018-159334 filed on Aug. 28, 2018 and Japanese Patent Application No. 2019-063408 filed on Mar. 28, 2019, the entire contents of which are incorporated herein by reference.

BACKGROUND

The disclosure relates to a driver interface, a robotic surgical apparatus including the driver interface, and a method of detecting attachment of a surgical instrument to the driver interface. More specifically, the disclosure relates to a driver interface provided for a robot arm of a robotic surgical system, a robotic surgical apparatus including the driver interface, and a method of detecting attachment of a surgical instrument to the driver interface.

Robotic surgical systems for assisting surgery are known. Such robotic surgical systems generally include a patient-side apparatus with robot arms and a remote control apparatus for remote control of the patient-side apparatus. To the robot arms of the patient-side apparatus, an endoscope and surgical instruments including forceps, for example, are attached. A doctor performs endoscopic surgery for the patient with robot arms of the patient-side apparatus by operating the remote control apparatus while checking patient endoscopic images. Using such a robotic surgical system minimizes the incision in the patient's skin, enabling minimally invasive surgery with the burden on the patient reduced.

In addition, a driver interface provided for a robot arm of such a robotic surgical system is known. U.S. Pat. No. 8,142,447 discloses an interface (a driver interface) provided for a robot arm of the robotic surgical system. This interface is connected to a tool (a surgical instrument) through an adaptor and is configured to transmit drive to the tool through the adaptor. The tool is detachably connected to the interface of the robot arm through the adaptor.

SUMMARY

Herein, in the case of detachably connecting a surgical instrument (tool) to the robot arm through the adaptor like the tool described in U.S. Pat. No. 8,142,447, the surgical instrument needs to be reliably attached to the robot arm through the adaptor. In order to confirm whether the surgical instrument is reliably attached to the robot arm, it is necessary to detect attachment of the surgical instrument to the robot arm.

An object of an embodiment of this disclosure is to provide a driver interface capable of reliably detecting attachment of a surgical instrument to a robot arm with a simple method, a robotic surgical apparatus including the driver interface, and a method of detecting attachment of the surgical instrument to the driver interface.

A first aspect of the disclosure may be a driver interface provided to a robot arm of a robotic surgical system for transmitting drive to a surgical instrument through a drive transmission member rotatably provided in an adaptor.

The driver interface may include: an engagement member which is rotatable about a rotation axis parallel to a rotation axis of the drive transmission member, wherein the engagement member includes an engagement protrusion protruding from a surface of the engagement member and provided corresponding to an engagement recess provided at the drive transmission member of the adaptor; an actuator which rotates the engagement member; a detection member movable with respect to the engagement member in a direction parallel to the rotation axis of the engagement member; and a sensor which is configured to detect the detection member that has moved as a result of contact with a part of the drive transmission member.

A second aspect of the disclosure may be a robotic surgical apparatus that may include: an adaptor including a drive transmission member rotatably provided therein; and a robot arm which includes a driver interface to which a surgical instrument is to be attached with the adaptor interposed therebetween and which transmits drive to the surgical instrument through the drive transmission member, wherein the drive transmission member includes an engagement recess.

The driver interface according to the second aspect may include: an engagement member which is rotatable about a rotation axis parallel to a rotation axis to the drive transmission member, wherein the engagement member includes an engagement protrusion protruding from a surface of the engagement member and provided corresponding to an engagement recess of the drive transmission member; an actuator which rotates the engagement member; a detection member movable with respect to the engagement member in a direction parallel to the rotation axis of the engagement member; and a sensor which detects the detection member that has moved as a result of contact with a part of the drive transmission member.

A third aspect of the disclosure may be a method of detecting attachment of a surgical instrument to a driver interface provided to a robot arm.

The method according to the third aspect may include: attaching the surgical instrument on an adaptor attached to the driver interface; moving a part of a drive transmission member rotatably provided in the adaptor, in a first direction parallel to a rotation axis of the drive transmission member; bringing the part of the drive transmission member moved in the first direction, into contact with a detection member provided to the driver interface to move the detection member in the first direction; and detecting the movement of the detection member in the first direction.

BRIEF DESCRIPTION OF DRAWINGS

FIG. 9A is a diagram illustrating a schematic view of a driver of the driver interface according to a first embodiment.

FIG. 9B is a diagram illustrating an exploded perspective view of the driver of the driver interface according to a first embodiment.

FIG. 11 is a diagram illustrating a schematic cross-sectional view of a state where the adaptor is mounted on the driver interface but is not engaged with the same according to a first embodiment with the table illustrating the detection results of sensors thereof.

FIG. 12 is a diagram illustrating a schematic cross-sectional view of a state where the adaptor is mounted on the driver interface and is engaged with the same according to a first embodiment with the table illustrating the detection results of sensors thereof.

FIG. 13 is a diagram illustrating a schematic cross-sectional view of a state where the surgical instrument is mounted on the driver interface but is not engaged according to a first embodiment with the table illustrating the detection results of sensors thereof.

FIG. 21 is a diagram illustrating a schematic cross-sectional view of a state where the surgical instrument is mounted on the driver interface but is not engaged with the same according to a second embodiment with the table illustrating the detection results of sensors thereof.

FIG. 23 is a diagram illustrating a schematic cross-sectional view illustrating a state where an adaptor and a surgical instrument are not mounted on a driver interface according to a modification of a second embodiment with a table illustrating detection results of sensors thereof.

DETAILED DESCRIPTION

Figure 1:
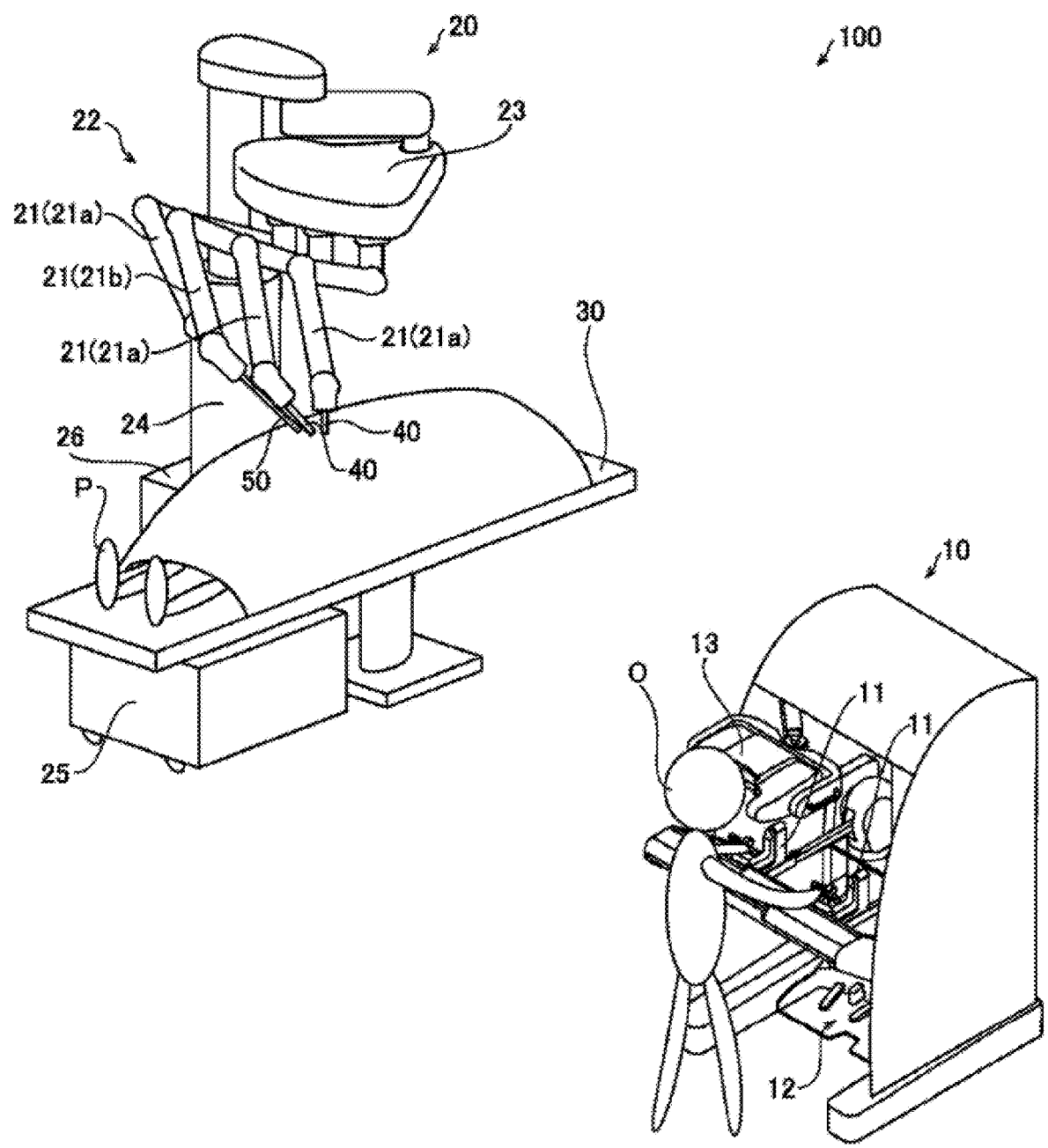
FIG. 1 is a diagram illustrating an overview of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

The configuration of a robotic surgical system 100 according to a first embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 and an endoscope 50, attached to robot arms 21. This allows for minimally invasive surgery.

The patient-side apparatus 20 constitutes an interface to perform a surgery for a patient P. The patient-side apparatus 20 is positioned beside an operation table 30 on which the patient P is laid. The patient-side apparatus 20 includes plural robot arms 21. One of the robot arms 21 (21*b*) holds the endoscope 50 while the other robot arms 21 (21*a*) hold the surgical instruments 40. The robot arms 21 are commonly supported by a platform 23. Each of the plural robot arms 21 includes plural joints. Each joint includes a driver provided with a servo-motor and a position detector such as an encoder. The robot arms 21 are configured so that the medical equipment attached to each robot arm 21 is controlled by a driving signal given through the controller 26 and performs a desired movement. The patient-side apparatus 20 is an example of a robotic surgical apparatus.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment is detachably attached to the distal ends of the robot arms 21a. Each surgical instrument 40 includes: a housing 43 (see FIG. 4), which is attached to the robot arm 21a; an elongated shaft 42 (see FIG. 4); and an end effector 41 (see FIG. 4), which is provided at the tip of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effector 41 of the surgical instrument 40 is then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
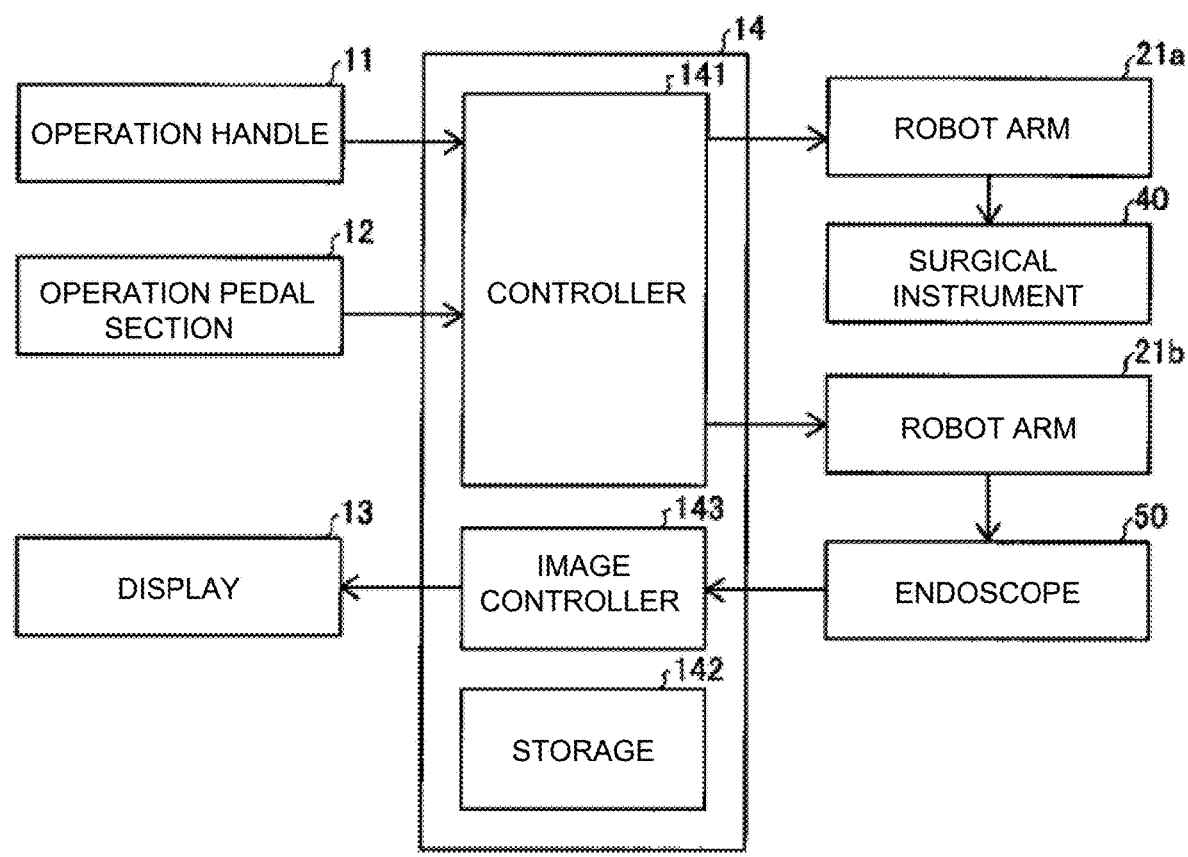
FIG. 2 is a block diagram illustrating a view of a control-related configuration of the robotic surgical system according to a first embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate medical equipment attached to the robot arms 21. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section on the master side in the master-slave system, and the robot arms 21a and 21b holding medical equipment constitute an operating section on the slave side. When the operator O operates the operation handles 11, the movement of one of the robot arms 21a or 21b is controlled so that the tip (the end effector 41 of the surgical instrument 40) of the robot arm 21a or the tip (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows for precise fine surgery.

The operation pedal section 12 includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21 to stop movement of the surgical instruments 40. Specifically, when the clutch pedal is being pressed, the robot arms 21 of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21. The operator O restarts the operation for the operation handles 11 around the center thereof.

The display section 13 or a display is configured to display images captured by the endoscope 50. The display section 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 50 attached to the robot arm 21b of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed.

(Configuration of Surgical Instrument, Adaptor, Drape, and Robot Arm)

With reference to FIGS. 3 to 14, the configurations of the surgical instrument 40, adaptor 60, drape 70, and robot arm 21 are described.

(Attachment Condition)

Figure 3:
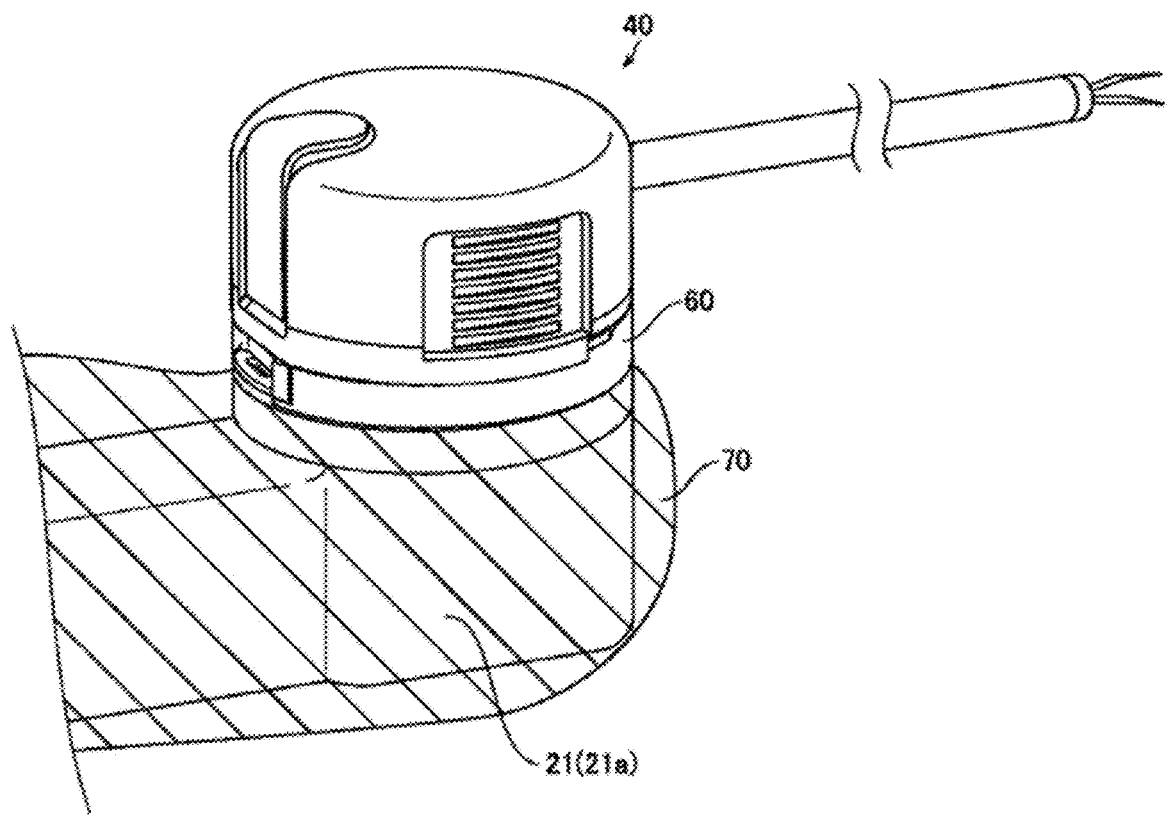
FIG. 3 is a diagram illustrating a perspective view of a state where a surgical instrument is attached to the robot arm through an adaptor according to a first embodiment.
Figure 4:
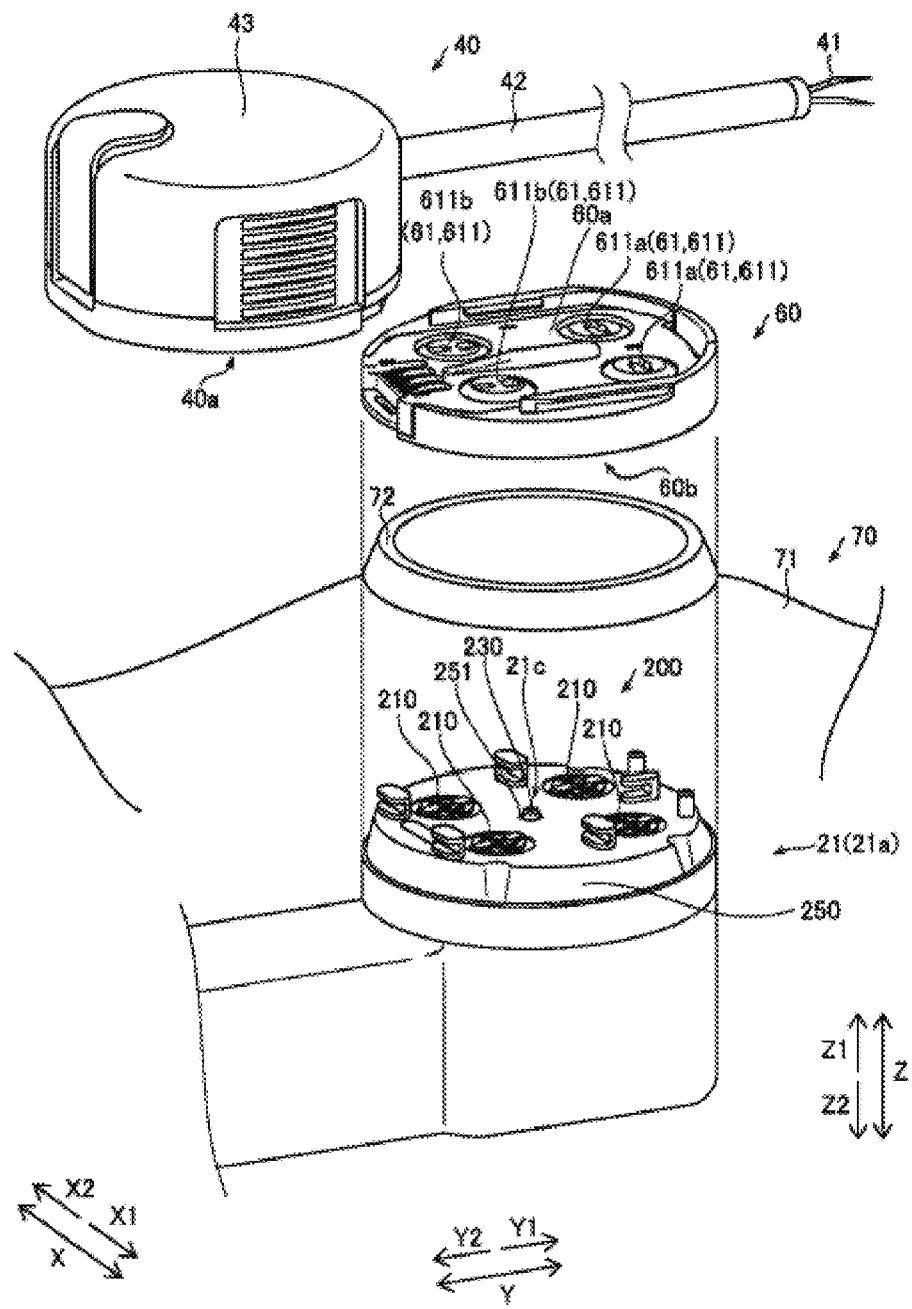
FIG. 4 is a diagram illustrating a perspective view of a state where the surgical instrument and the adaptor are detached from the robot arm according to a first embodiment.
Figure 5:
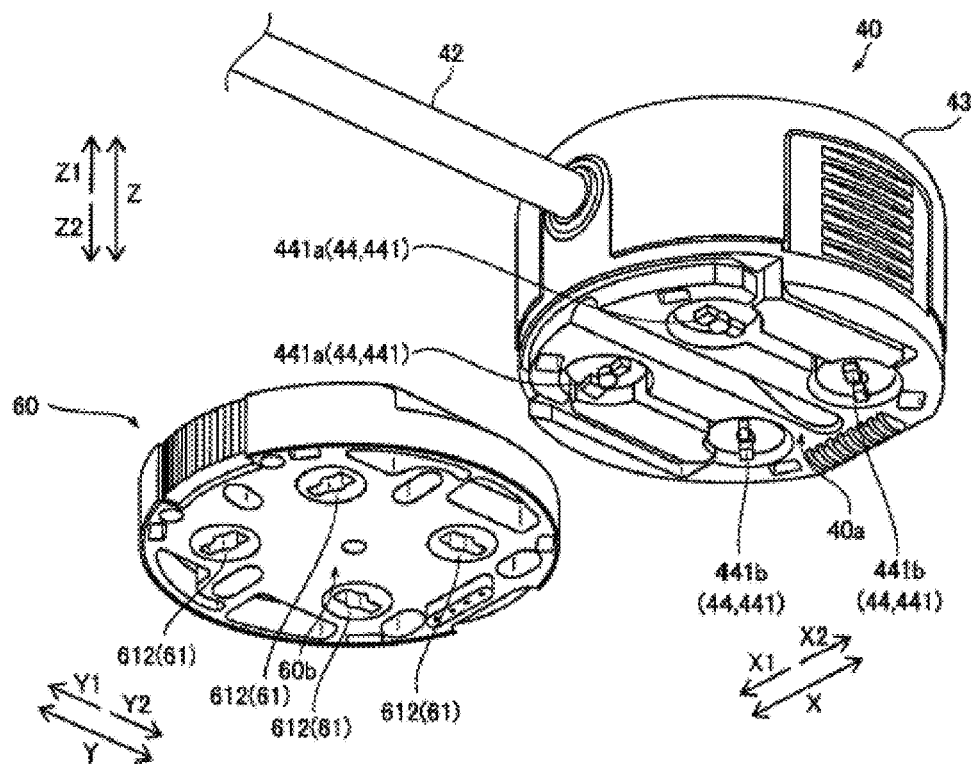
FIG. 5 is a diagram illustrating a perspective view of the adaptor and surgical instrument as seen in Z2 direction according to a first embodiment.

As illustrated in FIGS. 3 to 5, the surgical instrument 40 is detachably connected to the robot arm 21 through the adaptor 60. The adaptor 60 is a drape adaptor configured to sandwich a sterile drape 70 to cover the robot arm 21, in conjunction with the robot arm 21. The adaptor 60 is attached to an attachment surface 40a of a housing 43, on the Z2 side of the surgical instrument 40. The surgical instrument 40 is attached to an attachment surface 60a of the adaptor 60 on the Z1 side. The robot arm 21 is attached to an attachment surface 60b of the adaptor 60 on the Z2 side. The adaptor 60 is attached to an attachment surface 21c of the robot arm 21 on the Z1 side.

The robot arm 21 is used in a clean area and is covered with the drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 includes a body section 71 and an attachment section 72. The body section 71 covers the robot arm 21. The attachment section 72 is sandwiched between the robot arm 21 and adaptor 60. The body section 71 is made of a flexible film member. The flexible film member is made of a resin material, such as thermoplastic polyurethane and polyethylene. The body section 71 includes an opening so that the robot arm 21 is engaged with the adaptor 60. In the opening of the body section 71, the attachment section 72 is provided so as to close the opening. The attachment section 72 is made of a resin mold member. The resin mold member is made of a resin member such as polyethylene terephthalate. The attachment section 72 is harder (less flexible) than the body section 71. The attachment section 72 includes an opening so that the robot arm 21 is engaged with the adaptor 60. The opening of the attachment section 72 may be provided corresponding to the section where the robot arm 21 is engaged with the adaptor 60. The opening of the attachment section 72 may include plural openings corresponding to plural sections at which the robot arm 21 is engaged with the adaptor 60.

The surgical instrument 40 includes plural (four) driven members 44 (see FIG. 5), which are provided within the housing 43 and are rotatable about the respective rotation axes extending along the Z axis. The plural driven members 44 are provided to operate (drive) the end effector 41. For example, the driven members 44 are connected to the end effector 41 with wires (not illustrated) inserted through the shaft 42. The driven members 44 are rotated to drive the wires, which operate (drive) the end effector 41. In addition, the driven members 44 are connected to the shaft 42 through gears (not illustrated), for example. The shaft 42 is thereby rotated with rotation of the driven members 44.

To transmit driving force from the robot arm 21, the driven members 44 include engagement protrusions 441, which are engaged with later-described drive transmission members 61 of the adaptor 60. The engagement protrusions 441 protrude from the Z2-side surfaces of the respective driven members 44 toward the adaptor 60 (in the Z2 direction). The engagement protrusions 441 include engagement protrusions 441a, which are provided for the driven members 44 positioned on the Y1 side, and engagement protrusions 441b, which are provided for the driven members 44 positioned on the Y2 side. The engagement protrusions 441a are different in shape from the engagement protrusions 441b. The shapes of the engagement protrusions 441a and 441b correspond to engagement recesses 611a and 611b (described later) of the adaptor 60, respectively.

The adaptor 60 includes plural (four) drive transmission members 61, which are provided corresponding to the plural (four) driven members 44 of the surgical instrument 40. Each drive transmission member 61 is rotatable about a rotation axis A1 (see FIG. 6A), which extends along the Z axis. The drive transmission members 61 are provided to transmit driving force from the robot arm 21 to the driven members 44 of the surgical instrument 40. The drive transmission members 61 include engagement recesses 611 (see FIG. 4), which are engaged with the engagement protrusions 441 of the driven members 44 of the surgical instrument 40. Each engagement recess 611 is located in the surgical instrument 40 side (the Z1 side) of the drive transmission member 61 and is recessed from the Z1 side surface of the drive transmission member 61, in the Z2 direction, opposite to the surgical instrument 40. The engagement recesses 611 include engagement recesses 611a, which are provided for the drive transmission members 61 positioned on the Y1 side, and engagement recesses 611b, which are provided for the drive transmission members 61 positioned on the Y2 side. The engagement recesses 611a are different in shape from the engagement recesses 611b.

Each drive transmission member 61 includes the engagement recess 612 (see FIG. 5), which is engaged with first and second engagement protrusions 211a and 211b (described later) of the robot arm 21. The engagement recess 612 is located in the robot arm 21 side (on the Z2 side) of the drive transmission member 61 and is recessed from the Z2 side surface of the drive transmission member 61, in the Z1 direction, opposite to the robot arm 21. The plural drive transmission members 61 include substantially the same configuration excepting that the engagement recesses 611a are different in shape from the engagement recesses 611b.

Figure 6A:
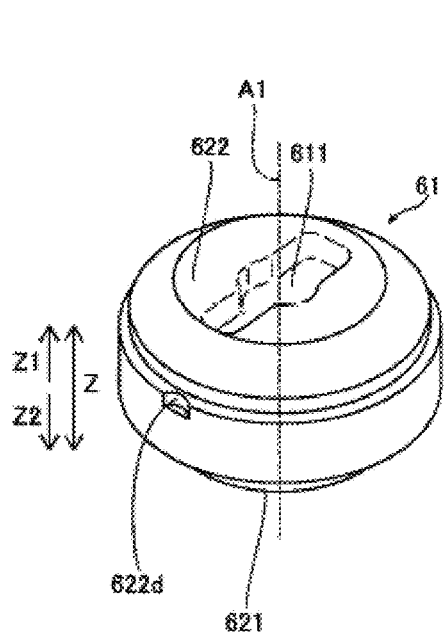
FIG. 6A is a diagram illustrating a perspective view of a drive transmission member of the adaptor according to a first embodiment.
Figure 6B:
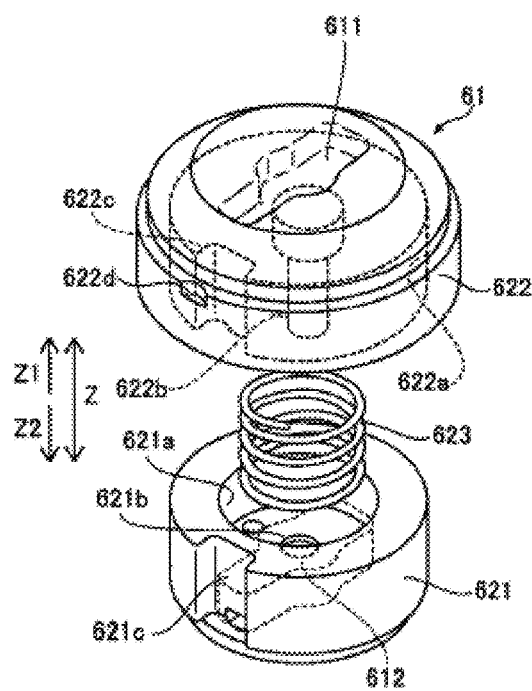
FIG. 6B is a diagram illustrating an exploded perspective view of the drive transmission member of the adaptor according to a first embodiment.

As illustrated in FIGS. 6A and 6B, each of the drive transmission members 61 includes a first member 621, which includes the engagement recess 612, and a second member 622, which includes the engagement recess 611. The first member 621 is positioned in the attachment surface 60b side (in the Z2 side). The second member 622 is positioned in the attachment surface 60a side (in the Z1 side). The second member 622 includes a fitting recess 622a, which is fitted on the first member 621. The first member 621 includes an accommodation recess 621a that accommodates a spring 623. The first member 621 and the second member 622 are fitted to each other along the Z axis with the spring 623 interposed therebetween. The drive transmission member 61 illustrated in FIGS. 6A and 6B includes the engagement recess 611a. The spring 623 is an example of a second spring.

The first member 621 is movable along the Z-axis relative to the second member 622 with the spring 623. In the process of attaching the adaptor 60 to the robot arm 21, the first member 621 of the drive transmission member 61 is movable so as to retract in the Z1 direction. The second member 622 is provided so as to move along the Z axis relative to the first member 621 with the spring 623. In the process of attaching the surgical instrument 40 to the adaptor 60, the second member 622 of the drive transmission member 61 is movable so as to retract in the Z2 direction. The spring 623 energizes the first member 621 in the Z2 direction while energizing the second member 622 in the Z1 direction. The spring 623 is a compression spring (a compression coil spring).

The first member 621 includes a through-hole 621b, which is provided within the engagement recess 612. The through-hole 621b penetrates the first member 621 in the rotation axis direction (along the Z axis). The through-hole 621b is substantially circular as seen in the rotation axis direction. The second member 622 includes an insertion section 622b, which is inserted into the through-hole 621b of the first member 621 along the Z axis. The insertion section 622b is inserted into the through-hole 621b to come into contact with a later-described detection member 213 (see FIG. 13) and press the detection member 213 in the Z2 direction. The insertion section 622b is extended along the Z axis. The insertion section 622b is substantially columnar. The through-hole 621b of the first member 621 and the insertion section 622b of the second member 622 are provided at the center of rotation of the drive transmission member 61.

The first and second members 621 and 622 are configured to together rotate about the rotation axis A1, which extends along the Z axis. Specifically, the first member 621 includes an engagement recess 621c, which is engaged with the second member 622 in the rotation direction. The second member 622 includes an engagement protrusion 622c, which is engaged with the first member 621 in the rotation direction. The engagement recess 621c is provided on the outer circumference of the first member 621 so as to be recessed inward. The engagement recess 621c is engaged with an engagement protrusion 622c of the second member 622. The engagement protrusion 622c is provided so as to protrude inward from the inner circumference (the fitting recess 622a) of the second member 622 and is engaged with the engagement recess 621c of the first member 621. The engagement recess 621c of the first member 621 and the engagement protrusion 622c of the second member 622 maintain the engagement therebetween even when the first or second member 621 or 622 moves in the Z1 or Z2 direction through the spring 623. In the drive transmission member 61, therefore, the first and second members 621 and 622 together rotate even when the first or second member 621 or 622 moves in the Z1 or Z2 direction.

Figure 7A:
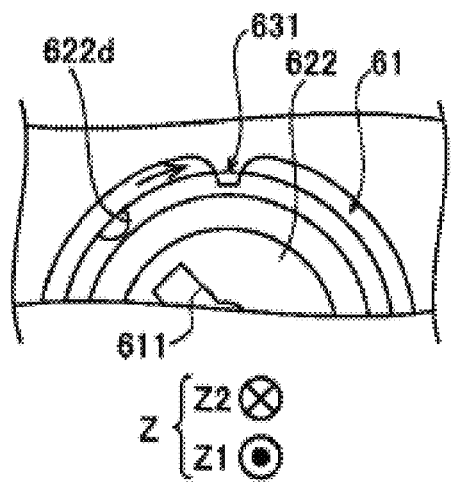
FIG. 7A is a diagram illustrating a schematic view of a state before a stopper section of the adaptor is engaged according to a first embodiment.
Figure 7B:
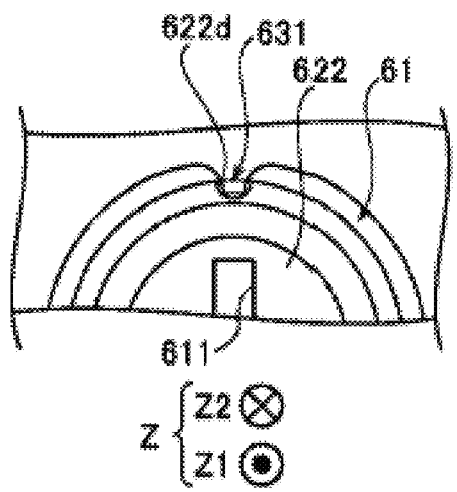
FIG. 7B is a diagram illustrating a schematic view of a state where the stopper section of the adaptor is engaged according to a first embodiment.

The second member 622 includes a stopper section 622d, which stops rotation of the drive transmission member 61 in the process of attaching the adaptor 60 to the robot arm 21. The stopper section 622d is provided as a notch on the outer circumference of the second member 622. As illustrated in FIGS. 7A and 7B, as the drive transmission member 61 is rotated, the stopper section 622d is engaged with a stopper engagement section 631 that is provided for the adaptor 60. The stopper section 622d is engaged with the stopper engagement section 631 to stop rotation of the drive transmission member 61. The stopper section 622d is configured to be engaged with the stopper engagement section 631 only when the drive transmission member 61 is rotated in a state that the second member 622 is located at farthest position in the Z1 direction. When the drive transmission member 61 is rotated in a state that the second member 622 is located on the Z2 direction side of the farthest position in the Z1 direction, the stopper section 622d is away from the stopper engagement section 631 on the Z axis and is not engaged with the stopper engagement section 631.

Figure 8:
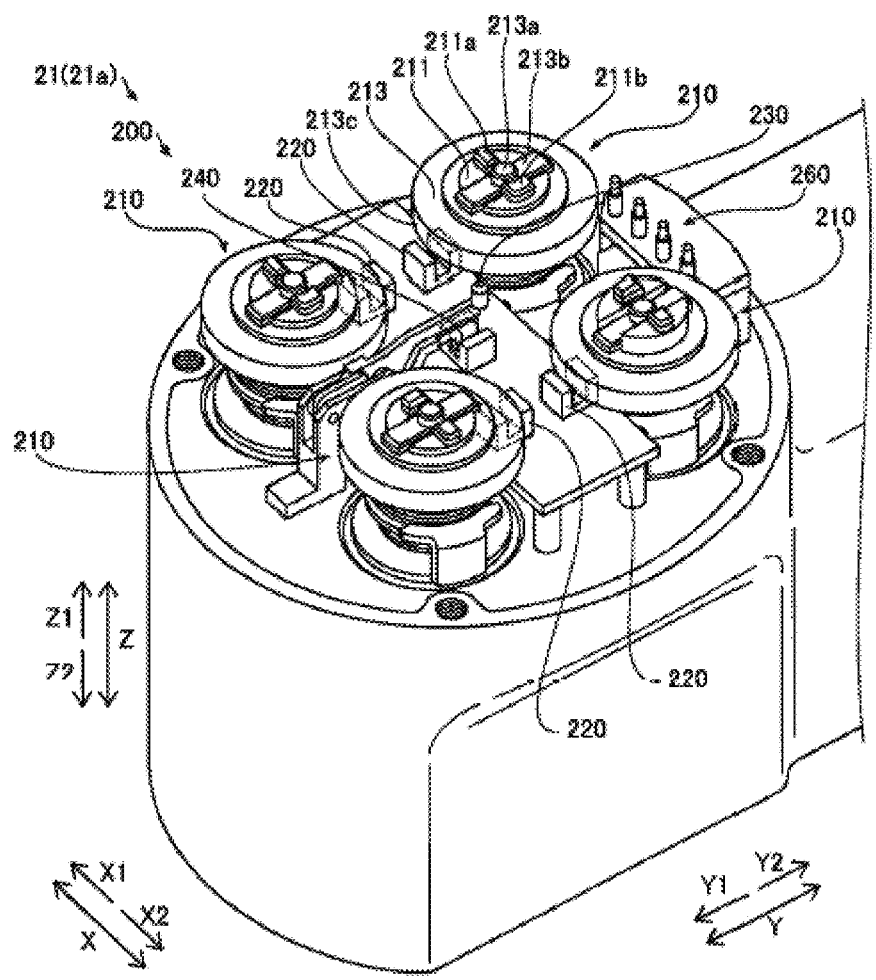
FIG. 8 is a diagram illustrating a schematic view of a state where a housing of the driver interface of the robot arm is removed according to a first embodiment.

As illustrated in FIGS. 4 and 8, the robot arm 21 includes a driver interface 200 to transmit drive to the surgical instrument 40 through the drive transmission members 61 of the adaptor 60. The driver interface 200 generates driving force to drive the end effector 41 of the surgical instrument 40. The driver interface 200 includes: plural (four) drivers 210, which are provided corresponding to the plural (four) drive transmission members 61 of the adaptor 60; and plural (four) sensors 220, which are provided corresponding to the plural (four) drivers 210.

Figure 10:
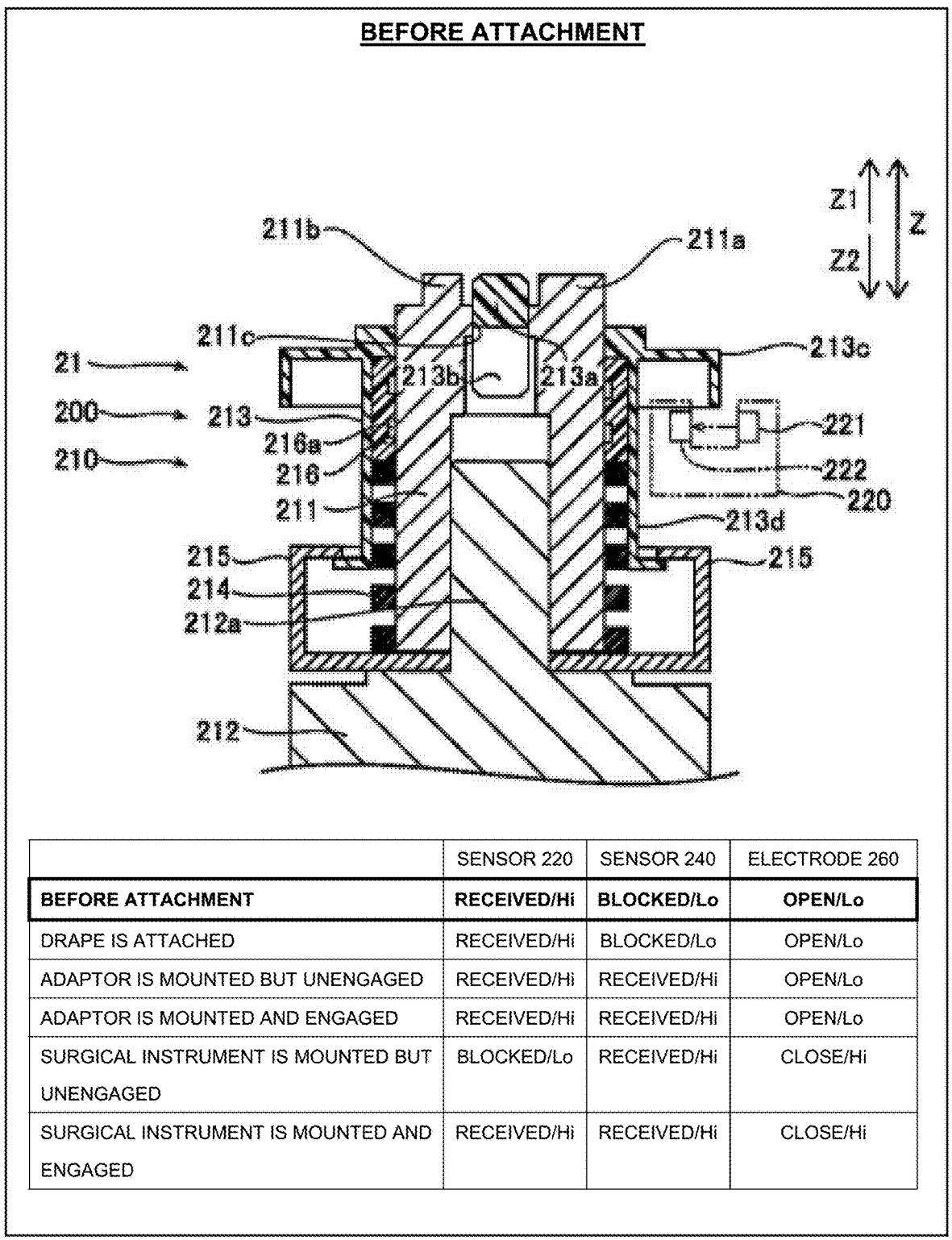
FIG. 10 is a diagram illustrating a schematic cross-sectional view of a state where the adaptor and surgical instrument are not mounted on the driver interface according to a first embodiment with a table illustrating detection results of sensors thereof.

As illustrated in FIGS. 9A, 9B, and 10, each of the drivers 210 includes an engagement member 211, an actuator 212, a detection member 213, a spring 214, and a pair of stopper members 215, and a bearing 216. The engagement member 211 is engaged with the corresponding drive transmission members 61 of the adaptor 60. The engagement member 211 includes a first engagement protrusion 211a and a second engagement protrusion 211b that are provided corresponding to the engagement recess 612 of the drive transmission member 61. The first and second engagement protrusions 211a and 211b are protruded from the Z1-side surface of the engagement member 211 in the Z1 direction. The first and second engagement protrusions 211a and 211b are provided so as to face each other across the center of rotation of the engagement member 211. The first and second engagement protrusions 211a and 211b are examples of an engagement protrusion. The spring 214 is an example of a first spring.

The engagement member 211 includes a groove 211c. The groove 211c is recessed from the Z1-side surface of the engagement member 211, in the Z2 direction, opposite to the direction in which the first and second engagement protrusions 211a and 211b are protruded. The groove 211c is positioned between the first and second engagement protrusions 211a and 211b for provision of a part of the detection member 213 therein. The groove 211c is linear and extends in a direction substantially orthogonal to the direction in which the first and second engagement protrusions 211a and 211b are arranged as seen in the rotation axis direction (along the Z axis). The groove 211c is provided to guide movement of the detection member 213 along the Z axis. The groove 211c is an example of a guide section.

The actuator 212 includes a motor and is configured to rotate the engagement member 211 about a rotation axis A2 that extends along the Z axis, in order to rotate the drive transmission member 61 about the rotation axis A1 that extends along the Z axis. The rotation axis A2 is parallel to and coincident with the rotation axis A1. The actuator 212 is connected to the engagement member 211 through a driving shaft 212a and transmits driving force to the engagement member 211 through the driving shaft 212a. The driving shaft 212a of the actuator 212 is connected to the engagement member 211 with a set screw (not illustrated).

The detection member 213 is provided so as to be detected by the corresponding sensor 220. The detection member 213 is provided so that at least a part thereof is positioned between the first and second engagement protrusions 211a and 211b. The detection member 213 is configured to move in a direction parallel to the rotation axis A2 of the engagement member 211 (hereinafter simply referred to as the Z1 or Z2 direction).

In a first embodiment, the sensor 220 detects the detection member 213 that has moved in the Z2 direction as a result of contact with a part (the insertion section 622b) of the second member 622 of the drive transmission member 61. By detecting the detection member 213 that has moved in the Z2 direction as a result of contact with the insertion section 622b of the second member 622, it is detected that the surgical instrument 40 is attached to the robot arm 21. This allows for detection of attachment of the surgical instrument 40 to the robot arm 21 by using a part (the insertion section 622b of the second member 622 of the drive transmission member 61) of the adaptor 60.

The sensor 220 is an optical sensor. The detection member 213 is easily detected by using a change in amount of received light due to movement of the detection member 213. Specifically, the sensor 220 is a transmission-type optical sensor including an emitter 221 (see FIG. 10) that emits light, and a receiver 222 (see FIG. 10) that receives the light from the emitter 221. The sensor 220 is configured to detect the detection member 213 upon light blockage due to a later-described detection portion 213c of the detection member 213. The detection member 213 is thereby detected easily and reliably in response to movement of the detection member 213. The sensor 220 is also configured to receive light when the light is not blocked by the detection portion 213c of the detection member 213. The sensor 220 detects High when the light is received and detects Low when the light is blocked.

The detection member 213 includes a contact section 213a, a guided section 213b, the detection portion 213c, and a cylinder 213d. The contact section 213a is arranged between the first and second engagement protrusions 211a and 211b and is configured to come into contact with the insertion section 622b of the second member 622 of the drive transmission member 61. This ensures the contact section 213a receive force applied by the insertion section 622b pressing the detection member 213 in the Z2 direction. The contact section 213a is provided at the position corresponding to the groove 211c of the engagement member 211. The contact section 213a thereby moves along the groove 211c as a guiding section. When the insertion section 622b comes into contact with the contact section 213a, the contact section 213a easily moves along the Z axis.

The contact section 213a is a contact protrusion that protrudes in the Z1 direction from the Z1-side surface of the detection member 213. The contact section 213a, which is a contact protrusion, more reliably receives force of the insertion section 622b pressing the detection member 213 in the Z2 direction. The contact section 213a, which is the contact protrusion, is provided so as to protrude in the Z1 direction to substantially the same position as the first and second engagement protrusions 211a and 211b. This prevents the contact section 213a as the contact protrusion from interfering with the engagement of the first and second engagement protrusions 211a and 211b with the engagement recess 612. The Z1-side surfaces of the contact section 213a and the first and second engagement protrusions 211a and 211b are substantially flush.

The detection member 213 is rotated about the rotation axis A2 that extends along the Z axis, together with the engagement member 211 by the actuator 212, and the contact section 213a is positioned at the center of rotation of the engagement member 211 and detection member 213. The contact section 213a is thereby located at the constant position even when the engagement member 211 and detection member 213 are rotated. This ensures the contact between the insertion section 622b and contact section 213a. The contact section 213a includes a shape corresponding to the insertion section 622b. Specifically, the contact section 213a is substantially circular as seen along the Z axis. The engagement member 211 is configured so as not to move along the Z axis. This simplifies the configuration of the engagement member 211 compared with the case where the engagement member 211 moves along the Z axis. The configuration of the driver 210 is therefore simplified.

The guided section 213b moves together with the contact section 213a. The guided section 213b is provided in the groove 211c of the engagement member 211 and is moved along the groove 211c as the guide section to move the detection member 213 in the Z1 or Z2 direction. This allows the detection member 213 to smoothly move in the Z1 or Z2 direction. The guided section 213b includes a shape corresponding to the groove 211c. Specifically, the guided section 213b is shaped in a liner bar.

The detection portion 213c is positioned outside the engagement member 211 and is configured to be detected by the sensor 220. This improves the flexibility in arrangement of the sensor 220 compared with the case where the detection portion 213c is positioned inside the engagement member 211. The detection portion 213c is annular. This keeps the positional relationship between the detection portion 213c and sensor 220 even when the engagement member 211 and detection member 213 are rotated. The detection portion 213c thereby continues to be located at the position where the detection portion 213c is detectable by the sensor 220.

The cylinder 213d is cylindrical and extends along the Z axis. The cylinder 213d faces the outer circumference of the engagement member 211. Between the inner circumference of the cylinder 213d and the outer circumference of the engagement member 211, the spring 214 and bearing 216 are positioned.

The spring 214 energizes the engagement member 211 in the Z1 direction. The spring 214 is a compression spring (a compression coil spring). The detection member 213 moves in the Z1 or Z2 direction relative to the engagement member 211 through the spring 214. The detection member 213 is thus able to move in the Z1 or Z2 direction with the simple configuration. The pair of stopper members 215 is configured to limit the movement of the detection member 213 in the Z1 direction through the spring 214. The stopper members 215 face each other with the detection member 213 interposed therebetween.

The bearing 216 is provided between the engagement member 211 and detection member 213 in order to reduce friction between the engagement member 211 and detection member 213. The bearing 216 is made of a resin material of a small coefficient of friction, such as fluorine resin. The bearing 216 includes a groove 216a that can accommodate a lubricant, such as grease. The groove 216a is circumferentially extended along the inner circumference of the bearing 216.

As illustrated in FIG. 8, the driver interface 200 includes a drape detection member 230 and a sensor 240 that is provided corresponding to the drape detection member 230. The drape detection member 230 and sensor 240 are provided to detect attachment of the drape 70. The drape detection member 230 is movable between a protruded position where the drape detection member 230 protrudes from the opening 251 (see FIG. 4) that is provided for the housing 250 of the robot arm 21, and a retracted position where the drape detection member 230 is retracted from the opening 251. The drape detection member 230 is positioned at the protruded position when the adaptor 60 and drape 70 are not mounted. The drape detection member 230 is moved to the retracted position when the adaptor 60 and drape 70 are mounted.

The sensor 240 is the same type of sensor as the sensors 220. When the adaptor 60 and drape 70 are not mounted, the drape detection member 230 located at the protruded position blocks the light in the sensor 240, and the sensor 240 detects Low. When the adaptor 60 and drape 70 are mounted, the drape detection member 230 moved to the retracted position does not block the light, and the sensor 240 receives the light and detects High.

The driver interface 200 includes an electrode section 260 for electrical connection with the surgical instrument 40. The electrode section 260 is electrically connected to an electrode section (not illustrated) of the surgical instrument 40 through an electrode section (not illustrated) of the adaptor 60. When the electrode section 260 is not connected to the electrode section of the surgical instrument 40 through the electrode section of the adaptor 60, Low is detected. When the electrode section 260 is connected to the electrode section of the surgical instrument 40 through the electrode section of the adaptor 60, High is detected. The electrode section 260 includes plural (four) electrodes.

(Detection of Attachment of Drape, Adaptor, and Surgical Instrument)

Next, with reference to FIGS. 10 to 14, detection of attachment of the drape 70, adaptor 60, and surgical instrument 40 to the robot arm 21 is described. The drape 70, adaptor 60, and surgical instrument 40 are attached to the robot arm 21 in this order. Changes of the states of the sensors 220 and 240 and electrode section 260 due to attachment of the drape 70, adaptor 60, and surgical instrument 40 are illustrated in tables of FIGS. 10 to 14.

FIG. 10 illustrates a state where the drape 70, adaptor 60, and surgical instrument 40 are not attached to the robot arm 21. In this state, the sensor 220 is in a light receiving state (High) because the detection member 213 does not block the light in the sensor 220. The sensor 240 is in a light blocked state (Low) because the drape detection member 230 blocks the light. The electrode section 260 is in an open state (Low) because the electrode section 260 is not connected to the electrode section of the surgical instrument 40. In the state where the drape 70 is attached to the robot arm 21 (not illustrated), the sensor 220, sensor 240, and electrode section 260 are in the same states as those illustrated in FIG. 10.

FIG. 11 illustrates a state where the drape 70 and adaptor 60 are mounted (positioned) on the robot arm 21 and the drive transmission member 61 of the adaptor 60 is not engaged with the driver 210. In this state, the sensor 220 is in the light receiving state (High) because the detection member 213 does not block the light in the sensor 220. On the other hand, the sensor 240 is in the light receiving state (High). This is because the adaptor 60 and drape 70 are mounted and move the drape detection member 230 from the protruded position to the retracted position, and the drape detection member 230 does not block the light in the sensor 240. It is thus detected that the adaptor 60 and drape 70 are mounted. The electrode section 260 is in an open state (Low) because the electrode section 260 is connected to the electrode section of the adaptor 60 but is not connected to the electrode section of the surgical instrument 40.

In this state, the first and second engagement protrusions 211a and 211b of the engagement member 211 of the driver 210 come into contact with the first member 621 of the drive transmission member 61. The first member 621 of the drive transmission member 61 is moved in the Z1 direction relative to the second member 622 through the spring 623. In the state where the first member 621 moved in the Z1 direction, the engagement member 211 of the driver 210 is rotated about the rotation axis A2 that extends along the Z axis. The first and second engagement protrusions 211a and 211b of the engagement member 211 of the driver 210 are moved to the position where the first and second engagement protrusions 211a and 211b are engageable with the engagement recess 612 of the drive transmission member 61. The first and second engagement protrusions 211a and 211b of the engagement member 211 of the driver 210 are thereby engaged with the engagement recess 612 of the drive transmission member 61. The first member 621 of the drive transmission member 61 is then moved in the Z2 direction relative to the second member 622 through the spring 623. The drive transmission member 61 is thereby rotatable about the rotation axis A1 that extends along the Z axis.

FIG. 12 illustrates a state where the drape 70 and adaptor 60 are mounted on the robot arm 21 and the drive transmission member 61 of the adaptor 60 is engaged with the driver 210. In this state, the sensor 220 is in the light receiving state (High) because the detection member 213 does not blocks the light in the sensor 220. The sensor 240 is in the light receiving state (High) because the drape detection member 230 does not block the light in the sensor 240. The electrode section 260 is in the open state (Low). This is because the electrode section 260 is connected to the electrode section of the adaptor 60 but is not connected to the electrode section of the surgical instrument 40.

In this state, the drive transmission member 61 is rotated about the rotation axis A1 that extends along the Z axis, as the engagement member 211 of the driver 210 is rotated. The second member 622 of the drive transmission member 61 is moved to the farthest position in the Z1 direction through the spring 623. When the drive transmission member 61 is rotated, the stopper section 622d of the drive transmission member 61 is engaged with the stopper engagement section 631 (see FIGS. 7A and 7B). This stops operation of the motor of the actuator 212 of the driver 210. It is thereby detected that the drape 70 and adaptor 60 are mounted on the robot arm 21 and the drive transmission member 61 of the adaptor 60 is engaged with the driver 210. In order to detect that motor operation of the actuator 212 is stopped, the encoder output of the motor is monitored, or the current value of the motor is monitored.

FIG. 13 illustrates a state where the surgical instrument 40 is further mounted (positioned) on the adaptor 60 attached to the robot arm 21 and the driven member 44 of the surgical instrument 40 is not engaged with the drive transmission member 61 of the adaptor 60. In this state, the detection member 213 is moved in the Z2 direction and blocks the light in the sensor 220. The sensor 220 is thereby in the light-blocked state (Low). The sensor 240 is in the light receiving state (High) because the drape detection member 230 does not block the light in the sensor 240. The electrode section 260 is in the closed state (High). This is because the electrode section 260 is connected to the electrode section of the surgical instrument 40 through the electrode section of the adaptor 60. It is thus detected that the surgical instrument 40 is mounted on the robot arm 21 but the driven member 44 of the surgical instrument 40 is not engaged with the drive transmission member 61 of the adaptor 60.

In this state, the engagement protrusion 441 of the driven member 44 is brought into contact with the second member 622 of the drive transmission member 61. The second member 622 of the drive transmission member 61 is thereby moved in the Z2 direction (a first direction) relative to the first member 621 through the spring 623. The insertion section 622b of the second member 622 is then moved in the Z2 direction to be inserted into the through-hole 621b of the first member 621. When the insertion section 622b of the second member 622 comes into contact with the contact section 213a, the detection member 213 is moved in the Z2 direction (the first direction) through the spring 214. The detection portion 213c of the detection member 213 thereby blocks the light in the sensor 220.

When the second member 622 is moved in the Z2 direction, the stopper section 622d and stopper engagement section 631 are separated on the Z axis and are disengaged from each other. The drive transmission member 61 is then rotated about the rotation axis A1 that extends along the Z axis. The engagement recess 611 of the drive transmission member 61 is moved to the position where the engagement recess 611 is engageable with the engagement protrusion 441 of the driven member 44. The engagement recess 611 of the drive transmission member 61 is then engaged with the engagement protrusion 441 of the driven member 44. The second member 622 of the drive transmission member 61 is thereby moved in the Z1 direction (a second direction) relative to the first member 621 through the spring 623. The detection member 213 is then moved in the Z1 direction (the second direction) through the spring 214.

Figure 14:
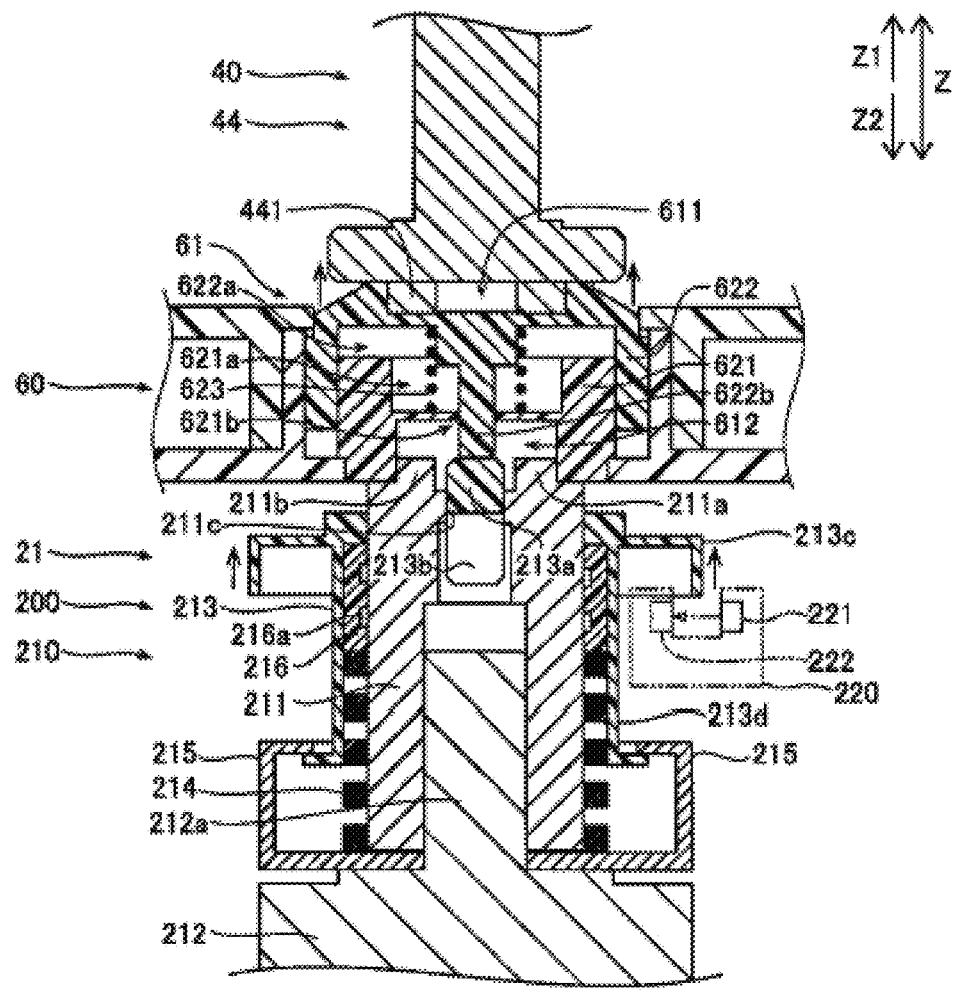
FIG. 14 is a diagram illustrating a schematic cross-sectional view of a state where the surgical instrument is mounted on the driver interface and is engaged with the same according to a first embodiment with the table illustrating the detection results of sensors thereof.

FIG. 14 illustrates a state where the surgical instrument 40 is mounted on the driver interface 200 of the robot arm 21 with the adaptor 60 interposed therebetween and the driven member 44 of the surgical instrument 40 is engaged with the drive transmission member 61 of the adaptor 60. In this state, the sensor 220 is in the light receiving state (High) because the detection member 213 is moved in the Z1 direction and does not block the light in the sensor 220. The sensor 240 is in the light receiving state (High) because the drape detection member 230 does not block the light in the sensor 240. The electrode section 260 is in the closed state (High) because the electrode section 260 is connected to the electrode section of the surgical instrument 40 through the electrode section of the adaptor 60. It is thus detected that the surgical instrument 40 is mounted on the robot arm 21 and the driven member 44 of the surgical instrument 40 is engaged with the drive transmission member 61 of the adaptor 60.

In this state, the engagement protrusion 441 of the driven member 44 comes into contact with the second member 622 of the drive transmission member 61, and the second member 622 of the drive transmission member 61 is moved to a position slightly short of the farthest position in the Z1 direction through the spring 623. The drive transmission member 61 is therefore rotatable, and the driven member 44 is also rotatable.

Second Embodiment

Next, a second embodiment is described with reference to FIGS. 15A to 22. In the second embodiment, an example where the drive transmission member further includes a pressing section is described, unlike the first embodiment. The same configurations of the second embodiment as those of the first embodiment are given the same reference numerals in the drawings, and the description thereof is omitted.

(Configuration of Robotic Surgical System)

Figure 15A:
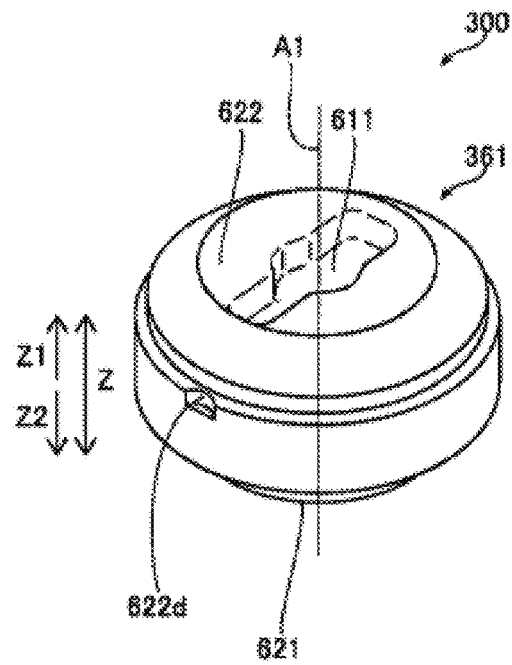
FIG. 15A is a diagram illustrating a perspective view of a drive transmission member of an adaptor according to a second embodiment.
Figure 15B:
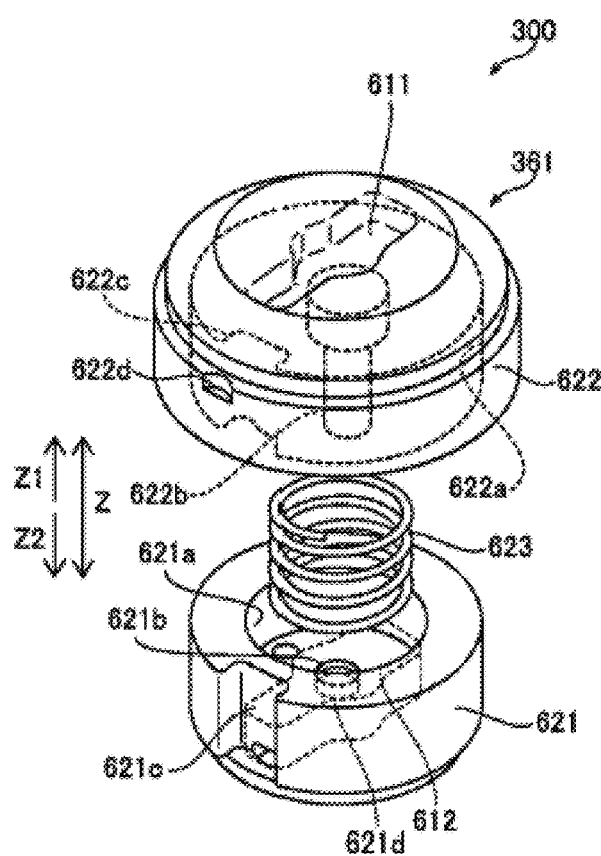
FIG. 15B is a diagram illustrating an exploded perspective view of the drive transmission member of the adaptor according to a second embodiment.

As illustrated in FIGS. 15A and 15B, a robotic surgical system 300 according to the second embodiment includes a drive transmission member 361, instead of the drive transmission member 61 of the first embodiment.

In the drive transmission member 361, the first member 621 further includes a pressing section 621d (see FIG. 15B).

The pressing section 621d is provided so as to come into contact with and press the detection member 213 of the driver 210 of the driver interface 200. Specifically, the pressing section 621d comes into contact with the contact section 213a of the detection member 213 and presses the detection member 213 in the Z2 direction. The pressing section 621d is provided so as to protrude from the through-hole 621b in the Z2 direction. The pressing section 621d is substantially cylindrical and extends along the Z axis. The substantially cylindrical pressing section 621d is formed so as to allow the insertion section 622b to be inserted therein through the through-hole 621b. The substantially cylindrical pressing section 621d and the substantially columnar insertion section 622b are provided in a concentric manner about the center of rotation of the detection member 213.

Figure 16:
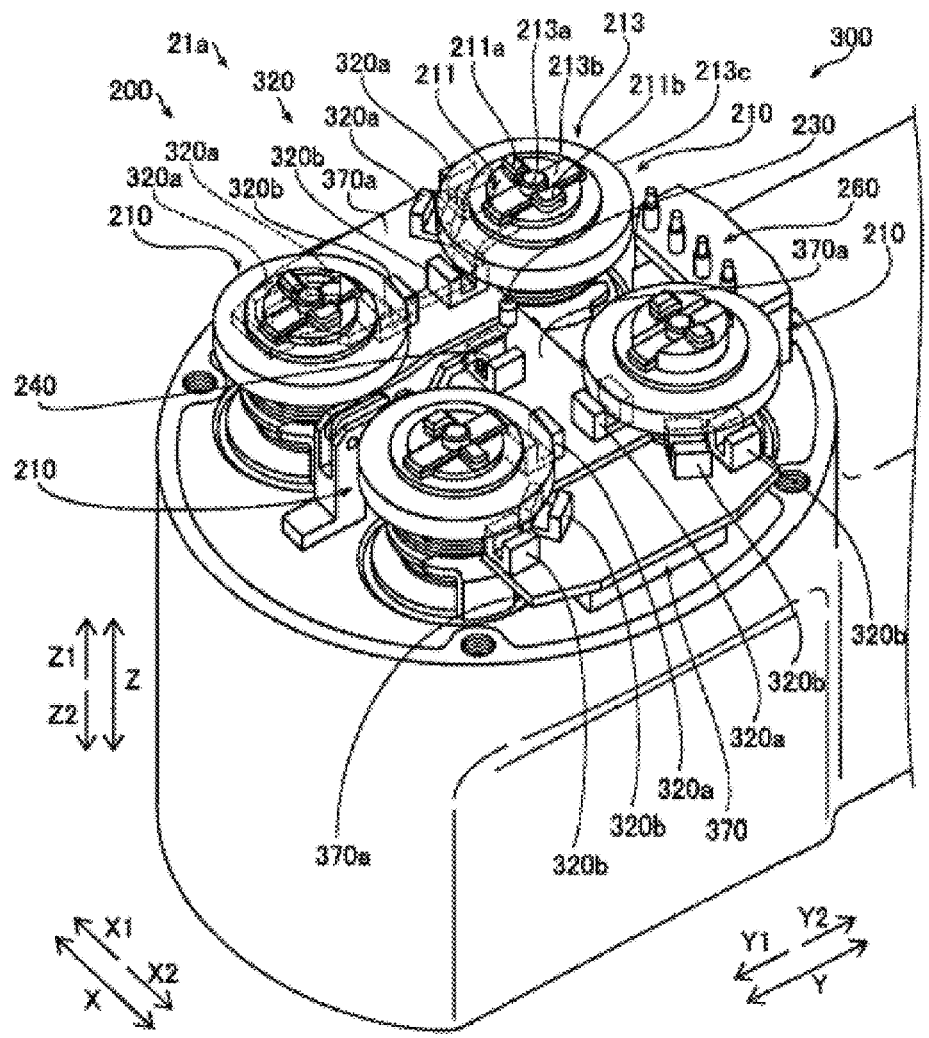
FIG. 16 is a diagram illustrating a perspective view of a state where a housing of a driver interface of the robot arm is removed according to a second embodiment.

The robotic surgical system 300 includes sensors 320, instead of the sensors 220 of the aforementioned first embodiment, as illustrated in FIG. 16. The sensors 320 include: sensors 320a to detect engagement between the adaptor 60 and surgical instrument 40; and sensors 320b to detect engagement between the adaptor 60 and robot arm 21. The sensors 320a include plural (eight) sensors 320a that are provided corresponding to the plural (four) drivers 210. Each of the plural drivers 210 is provided with two corresponding sensors 320a. The sensors 320b include plural (four) sensors 320b that are provided corresponding to the plural (four) drivers 210. Each of the plural drivers 210 is provided with one corresponding sensor 320b.

Figure 18:
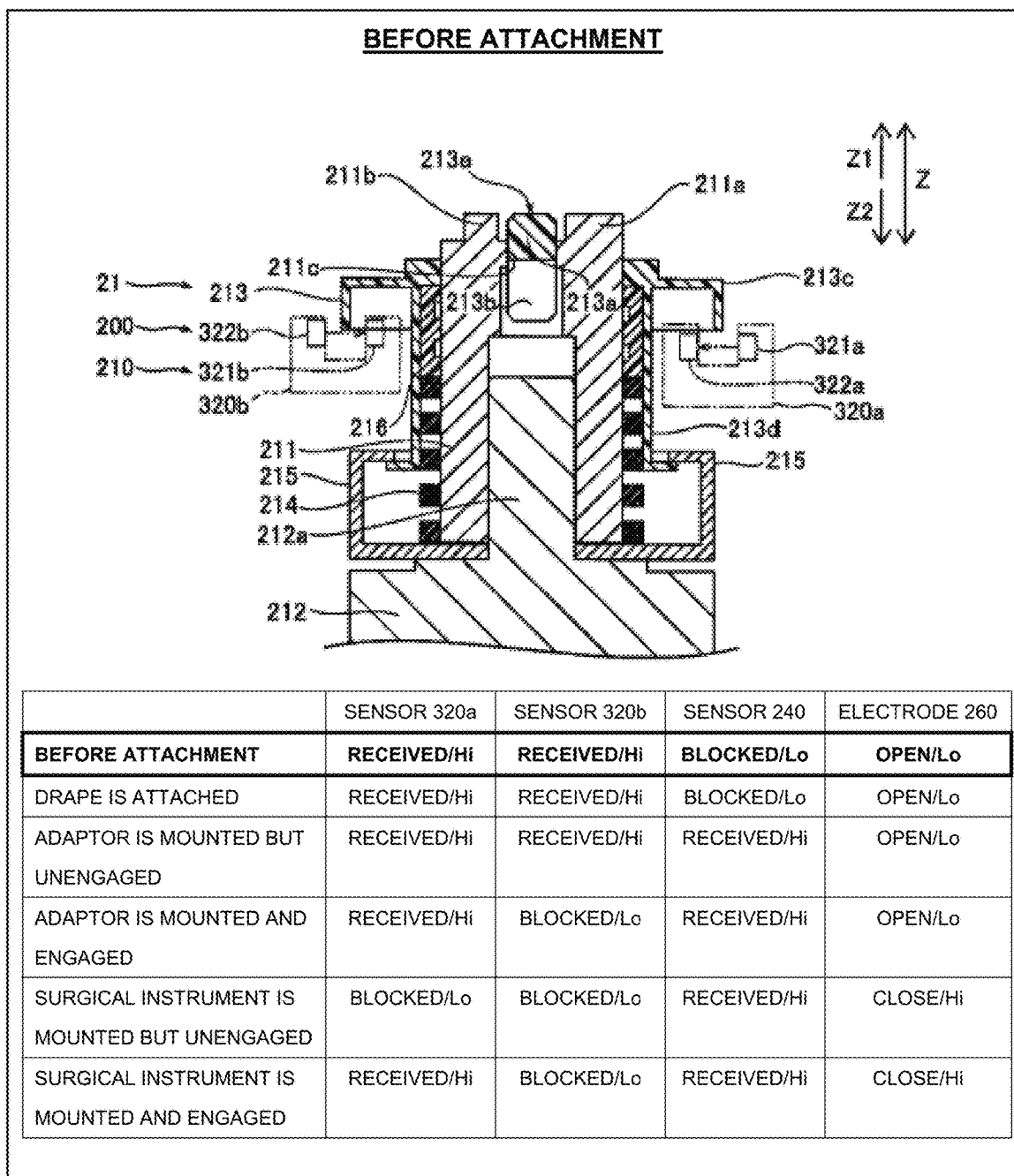
FIG. 18 is a diagram illustrating a schematic cross-sectional view of a state where the adaptor and surgical instrument are not mounted on the driver interface according to a second embodiment with a table illustrating the detection results of sensors thereof.

Each sensors 320a (320b) is a transmission-type optical sensor and includes an emitter 321a (322b) that emits light (see FIG. 18) and a receiver 322a (321b) that receives the light from the emitter 321a (322b) (see FIG. 18). The sensor 320a (320b) is configured to detect the detection member 213 based on light blockage due to the detection portion 213c of the detection member 213. The sensor 320a (320b) receives the light when the detection portion 213c of the detection member 213 does not block the light. The sensor 320a (320b) detects High when the light is received (the light is incident) and detects Low when the light is blocked.

In the second embodiment, the sensors 320a and 320b are configured to detect the detection members 213 at different moments. The sensors 320a thereby detect engagement between the adaptor 60 (the driver interface 200 of the robot arm 21) and surgical instrument 40 while the sensors 320b detect engagement between the adaptor 60 and robot arm 21. In the first embodiment, the engagement between the adaptor 60 and robot arm 21 is detected based on whether the operation of the motor of the actuator 212 is stopped. In the second embodiment, it is unnecessary to monitor the encoder output of the motor or the current value of the motor to determine whether the operation of the motor of the actuator 212 is stopped. The engagement between the adaptor 60 and robot arm 21 is therefore detected more easily. The sensors 320a and sensors 320b are examples of a first sensor and a second sensor, respectively.

The sensors 320a and sensors 320b detect the detection members 213 at different positions in the direction where the detection members 213 move (along the Z axis, in the direction along the rotation axis A2 of the engagement member 211). The sensors 320a and sensors 320b are thereby easily configured to detect the detection members 213 at different moments. The sensors 320a are positioned so as to detect the detection members 213 at a detection position lower than (on the Z2 side of) that at which the sensors 320b detect the same. The sensors 320b are positioned so as to detect the detection members 213 at a detection position higher than (on the Z1 side of) that at which the sensors 320a detect the same. The "higher" means "closer to the adaptor 60 on the Z axis (or farther in the Z1 direction)" while the "lower" means "farther from the adaptor 60 on the Z axis (or farther in the Z2 direction)".

The sensors 320a and sensors 320b are provided on a substrate section 370 as a circuit board, such as a printed circuit board. The substrate section 370 includes substrates 370a and a substrate 370b. On the substrates 370a, the sensors 320a are provided. On the substrate 370b, the sensors 320b are provided. The substrates 370a are located at a different height (a different position on the Z axis) from the substrate 370b in the direction in which the detection members 213 move. The sensors 320a and the sensors 320b are therefore easily configured to detect the detection members 213 at different positions in the direction in which the detection members 213 move. The substrate 370a includes a sensor mount surface where the sensors 320a are provided, and is provided such that the sensor mount surface of the substrate 370a is located at a lower position than (a position on the Z2 side) than sensor mount surfaces of the substrates 370b where the sensors 320b are provided. The substrate 370b includes a sensor mount surface where the sensors 320b are provided, and is provided such that the sensor mount surface of the substrate 370b is located at a higher position than (a position on the Z1 side) than sensor mount surfaces of the substrates 370a where the sensors 320a are provided. The substrates 370a and substrate 370b are examples of first and second substrates, respectively.

Figure 17A:
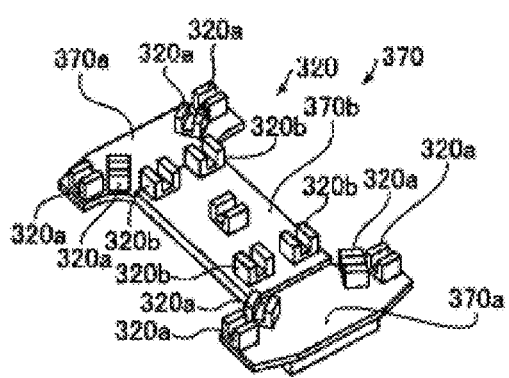
FIG. 17A is a diagram illustrating a schematic view illustrating an example of the second embodiment where a first substrate and a second substrate of a substrate section of the driver interface constitute an integrated structure.
Figure 17B:
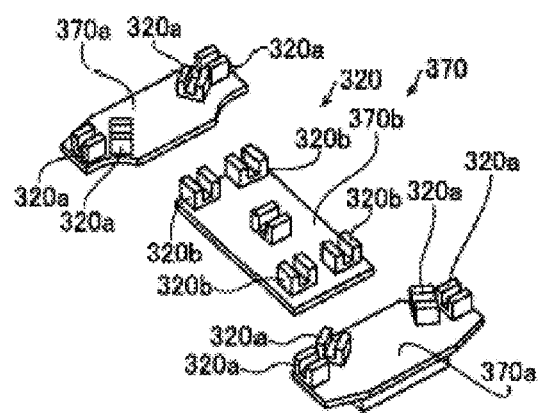
FIG. 17B is a diagram illustrating a schematic view illustrating an example of the second embodiment where the first and second substrates of the substrate section of the driver interface constituted a split.

As illustrated in FIGS. 17A and 17B, the substrates 370a and substrate 370b may constitute an integrated structure or constitute a split structure. In the integrated structure, the substrates 370a and substrate 370b constitute different portions of a circuit substrate including a height difference between each substrate 370a and the substrate 370b. In the split structure, the substrates 370a and substrate 370b are composed of circuit substrates independent of each other and are connected for use so as to form a height difference between each substrate 370a and the substrate 370b.

As illustrated in FIGS. 18 to 22, the sensor 320a detects the detection member 213 that has moved in the Z2 direction as a result of contact with the insertion section 622b. The sensor 320b detects the detection member 213 which has moved in the Z2 direction as a result of contact with the pressing section 621d. The sensor 320a thus detects movement of the second member 622 including the insertion section 622b of the drive transmission member 361, allowing for easy detection of the engagement between the adaptor 60 and surgical instrument 40. Furthermore, the sensor 320b detects movement of the first member 621 including the pressing section 621d of the drive transmission member 361, allowing for easy detection of engagement between the adaptor 60 and robot arm 21.

The detection member 213 includes a surface 213e that comes into contact with the pressing section 621d and insertion section 622b. The structure of the detection member 213 is thereby simplified compared with a case where the detection member 213 separately includes a contact surface that comes into contact with the pressing section 621d and a contact surface that comes into contact with the insertion section 622b. The surface 213e is the top surface of the contact section 213a as the contact protrusion and is flat. The surface 213e is provided so as to face the top surface of the pressing section 621d and the top surface of the insertion section 622b along the Z axis.

Figure 19:
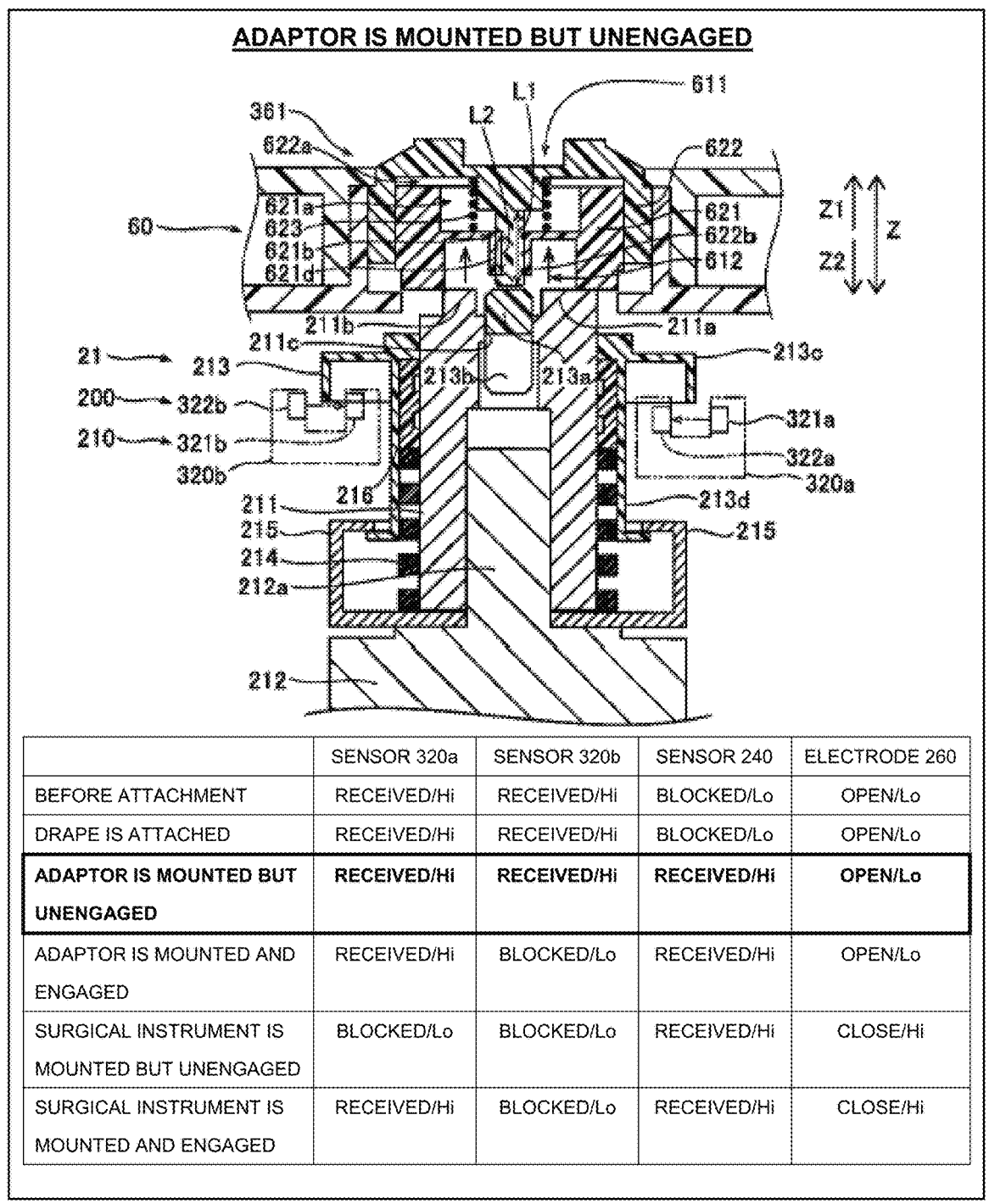
FIG. 19 is a diagram illustrating a schematic cross-sectional view of a state where the adaptor is mounted on the driver interface but is not engaged with the same according to a second embodiment with the table illustrating the detection results of sensors thereof.

In the direction in which the detection member 213 moves (along the Z axis), length L1 of the insertion section 622b (see FIG. 19) is greater than length L2 of the pressing section 621d (see FIG. 19). The detection member 213 that has moved as a result of contact with the pressing section 621d is further moved by the insertion section 622b that is longer than the pressing section 621d. The sensor 320a and sensor 320b are thus easily configured to detect the detection member 213 at different moments. The length L1 of the insertion section 622b is the distance between the proximal end and the distal end of the insertion section 622b on the Z axis. The length L2 of the pressing section 621d is the distance between the proximal end and the distal end of the pressing section 621d on the Z axis.

(Detection of Attachment of Drape, Adaptor, and Surgical Instrument)

Next, with reference to FIGS. 18 to 22, detection of attachment of the drape 70, adaptor 60, and surgical instrument 40 to the robot arm 21 is described. Changes in states of the sensors 320a, 320b, and 240 and electrode section 260 due to attachment of the drape 70, adaptor 60, and surgical instrument 40 are illustrated in tables of FIGS. 18 to 22.

FIG. 18 illustrates a state where the drape 70, adaptor 60, and surgical instrument 40 are not attached to the robot arm 21. In this state, the sensor 320a is in the light receiving state (High) because the detection member 213 does not block the light in the sensor 320a. The sensor 320b is in the light receiving state (High) because the detection member 213 does not block the light in the sensor 320b. The sensor 240 is in the light blocked state (Low) because the drape detection member 230 blocks the light in the sensor 240. Furthermore, the electrode section 260 is in the open state (Low) because the electrode section 260 is not connected to the electrode section of the surgical instrument 40. In the state where the drape 70 is positioned on the robot arm 21 (not illustrated), the sensors 320a, 320b, and 240 and electrode section 260 are in the same states as those illustrated in FIG. 18.

FIG. 19 illustrates a state where the drape 70 and adaptor 60 are mounted (positioned) on the robot arm 21 and the drive transmission member 361 of the adaptor 60 is not engaged with the driver 210. In this state, the sensor 320a is in the light receiving state (High) because the detection member 213 does not block the light in the sensor 320a. The sensor 320b is in the light receiving state (High) because the detection member 213 does not block the light in the sensor 320b. When the adaptor 60 and drape 70 are mounted, the drape detection member 230 is moved from the protruded position to the retracted position and does not block the light in the sensor 240. The sensor 240 is thereby in the light receiving state (High). It is thus detected that the adaptor 60 and drape 70 are mounted. The electrode section 260 is in the open state (Low) because the electrode section 260 is connected to the electrode section of the adaptor 60 but is not connected to the electrode section of the surgical instrument 40.

In this state, the first and second engagement protrusions 211a and 211b of the engagement member 211 of the driver 210 come into contact with the first member 621 of the drive transmission member 361. The first member 621 of the drive transmission member 361 is moved in the Z1 direction relative to the second member 622 through the spring 623. In the state where the first member 621 is moved in the Z1 direction, the engagement member 211 of the driver 210 is rotated about the rotation axis A2 that extends along the Z axis. The first and second engagement protrusions 211a and 211b of the engagement member 211 of the driver 210 are moved to the position where the first and second engagement protrusions 211a and 211b are engageable with the engagement recess 612 of the drive transmission member 361. The first and second engagement protrusions 211a and 211b of the engagement member 211 of the driver 210 are then engaged with the engagement recess 612 of the drive transmission member 361. The first member 621 of the drive transmission member 361 is then moved in the Z2 direction relative to the second member 622 through the spring 623. The drive transmission member 361 becomes rotatable about the rotation axis A1 that extends along the Z axis, with driving force from the driver 210.

Figure 20:
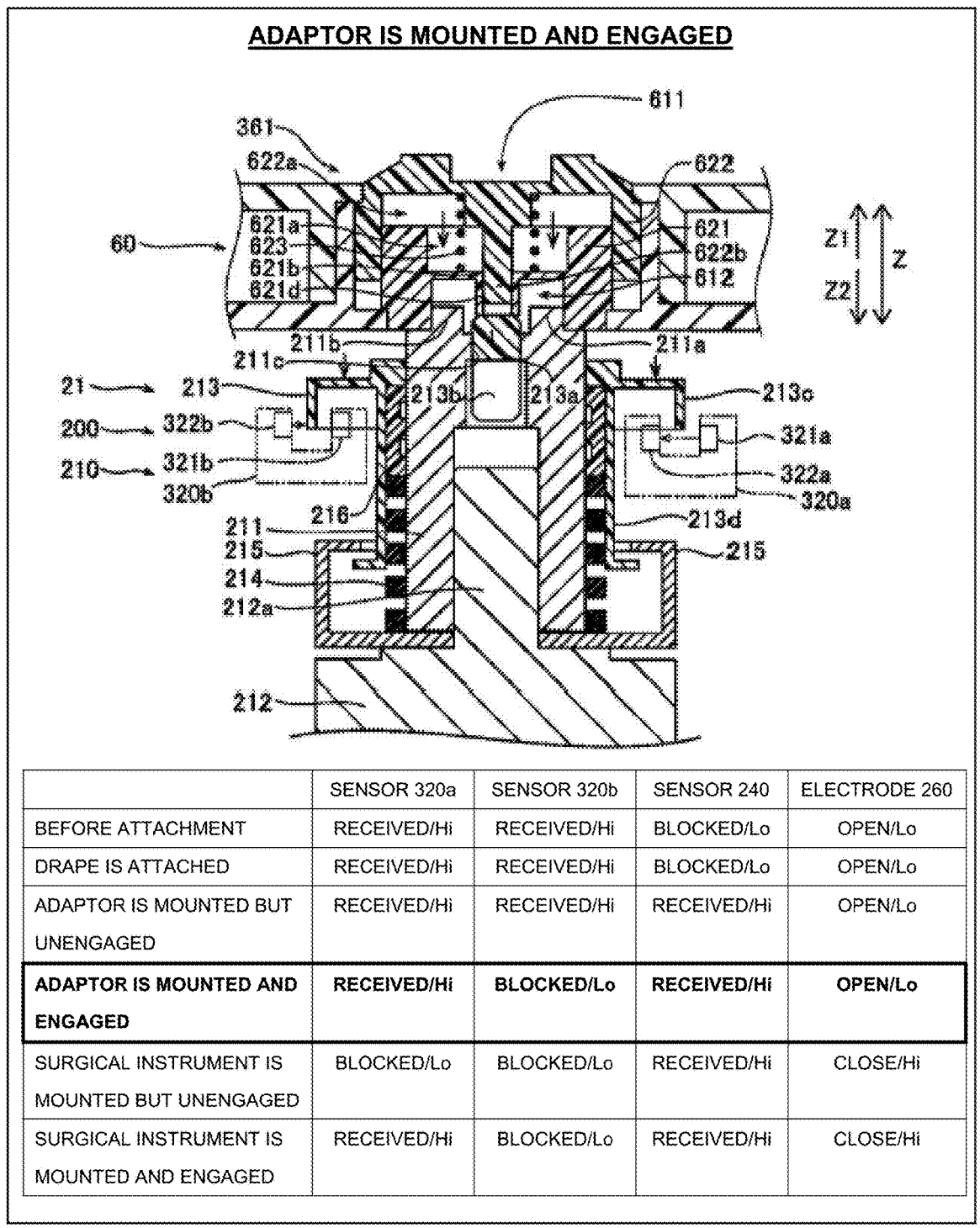
FIG. 20 is a diagram illustrating a schematic cross-sectional view of a state where the adaptor is mounted on the driver interface and is engaged with the same according to a second embodiment with the table illustrating the detection results of sensors thereof.

FIG. 20 illustrates a state where the drape 70 and adaptor 60 are mounted on the robot arm 21 and the drive transmission member 361 of the adaptor 60 is engaged with the driver 210. In this state, the sensor 320a is in the light receiving state (High) because the detection member 213 does not block the light in the sensor 320a. On the other hand, the sensor 320b is in the light blocked state (Low) because the detection member 213 is moved in the Z2 and blocks the light in the sensor 320b. It is thus detected that the drape 70 and adaptor 60 are mounted on the robot arm 21 and the drive transmission member 361 of the adaptor 60 is engaged with the engagement member 211 of the driver 210. The sensor 240 is in the light receiving state (High) because the drape detection member 230 does not block the light in the sensor 240. The electrode section 260 is in the open state (Low) because the electrode section 260 is connected to the electrode section of the adaptor 60 but is not connected to the electrode section of the surgical instrument 40.

In this state, the engagement member 211 of the driver 210 is engaged with the first member 621 of the drive transmission member 361, and the first member 621 of the drive transmission member 361 is thereby moved in the Z2 direction relative to the second member 622 through the spring 623. The pressing section 621d of the 621 then comes into contact with the detection member 213. The detection member 213 is thereby moved in the Z2 direction through the spring 214. The detection portion 213c of the detection member 213 blocks the light in the sensor 320b.

FIG. 21 illustrates a state where the surgical instrument 40 is further mounted (positioned) on the adaptor 60 attached to the robot arm 21 and the driven member 44 of the surgical instrument 40 is not engaged with the drive transmission member 361 of the adaptor 60. In this state, the sensor 320a is in the light blocked state (Low) because the detection member 213 is moved in the Z2 direction and blocks the light in the sensor 320a. The sensor 320b is in the light blocked state (Low) because the detection member 213 blocks the light in the sensor 320b. The sensor 240 is in the light receiving state (High) because the drape detection member 230 does not block the light in the sensor 240. The electrode section 260 is therefore in the closed state (High) because the electrode section 260 is connected to the electrode section of the surgical instrument 40 through the electrode section of the adaptor 60. It is thus detected that the surgical instrument 40 is mounted on the robot arm 21 and the driven member 44 of the surgical instrument 40 is not engaged with the drive transmission member 361 of the adaptor 60.

In this state, the engagement protrusion 441 of the driven member 44 is brought into contact with the second member 622 of the drive transmission member 361. The second member 622 of the drive transmission member 361 is moved in the Z2 direction relative to the first member 621 through the spring 623. The insertion section 622*b* of the second member 622 is thereby moved in the Z2 direction to be inserted into the through-hole 621*b* and pressing section 621*d* of the first member 621. In the state where the insertion section 622*b* is moved in the Z2 direction, the top end of the insertion section 622*b* is located at the farther position in the Z2 direction than the top end of the pressing section 621*d*. Only the insertion section 622*b*, among the insertion section 622*b* and pressing section 621*d*, comes into contact with the detection member 213. The detection member 213 is thereby moved in the Z2 direction through the spring 214. The detection portion 213*c* of the detection member 213 therefore blocks the light in the sensor 320*a*.

In this state, the drive transmission member 361 is rotated about the rotation axis A1 that extends along the Z axis, by the driving force from the driver 210. The engagement recess 611 of the drive transmission member 361 is moved to the position where the engagement recess 611 of the drive transmission member 361 is engageable with the engagement protrusion 441 of the driven member 44. The engagement recess 611 of the drive transmission member 361 is then engaged with the engagement protrusion 441 of the driven member 44. The second member 622 of the drive transmission member 361 is thereby moved in the Z1 direction relative to the first member 621 through the spring 623. The driven member 44 becomes rotatable about the rotation axis extending along the Z axis, through the drive transmission member 361 with the driving force from the driver 210. The detection member 213 is moved in the Z1 direction through the spring 214 (returned to the position where the detection member 213 is in contact with the pressing section 621*d*).

Figure 22:
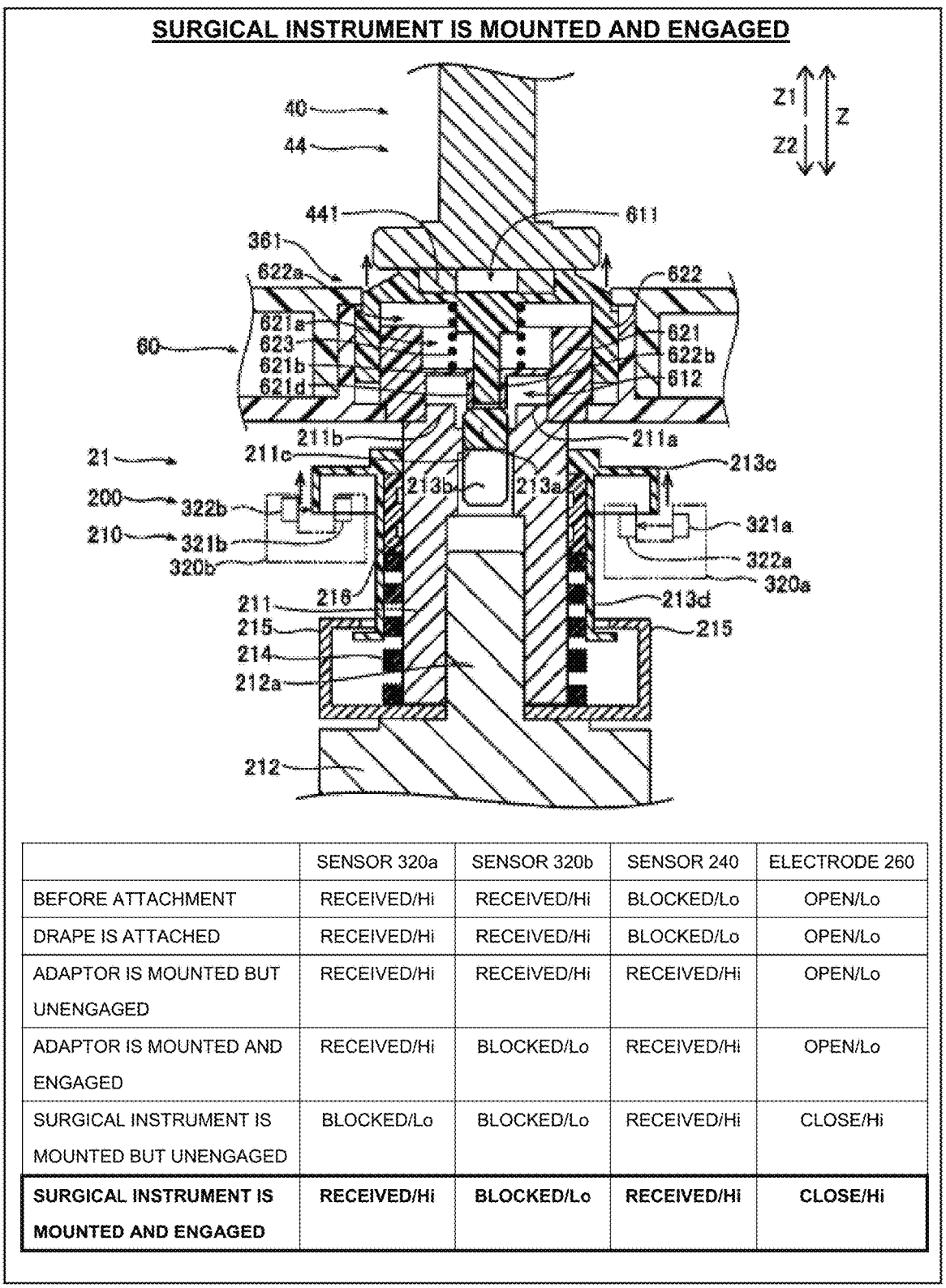
FIG. 22 is a diagram illustrating a schematic cross-sectional view of a state where the surgical instrument is mounted on the driver interface and is engaged with the same according to a second embodiment with the table illustrating the detection results of sensors thereof.

FIG. 22 illustrates a state where the surgical instrument 40 is mounted on the driver interface 200 of the robot arm 21 with the adaptor 60 interposed therebetween and the driven member 44 of the surgical instrument 40 is engaged with the drive transmission member 361 of the adaptor 60. In this state, the sensor 320*a* is in the light receiving state (High) because the detection member 213 is moved in the Z1 direction and does not block the light in the sensor 320*a*. The sensor 320*b* is in the light blocked state (Low) because the detection member 213 blocks the light in the sensor 320*b*. The sensor 240 is in the light receiving state (High) because the drape detection member 230 does not block the light in the sensor 240. The electrode section 260 is in the closed state (High) because the electrode section 260 is connected to the electrode section of the surgical instrument 40 through the electrode section of the adaptor 60. It is thus detected that the surgical instrument 40 is mounted on the robot arm 21 and the driven member 44 of the surgical instrument 40 is engaged with the drive transmission member 361 of the adaptor 60.

Modification

It should be understood that the embodiments disclosed herein are illustrated by way of example in every respect and not limit the invention. The scope of the invention is indicated by claims, not by explanation of the embodiments, and includes equivalents to claims and all alterations within the same.

For example, the sensors are optical sensors in the examples illustrated in the first and second embodiments, but the disclosure is not limited thereto. In the disclosure, the sensors may be sensors other than optical sensors. The sensors may be switches such as microswitches.

The contact sections are contact protrusions in the examples illustrated in the first and second embodiments, but the disclosure is not limited thereto. In the disclosure, the contact sections are unnecessarily contact protrusions. The contact sections may be contact recesses which are recessed from the surfaces of the detection members, for example.

The detection members are rotated with the engagement members in the examples illustrated in the first and second embodiments, but the disclosure is not limited thereto. In the disclosure, the detection members are unnecessarily rotated together with the engagement members.

The adaptor and drape are provided independently of each other in the examples illustrated in the first and second embodiments, but the disclosure is not limited thereto. In the disclosure, the adaptor and drape may be provided integrally, or the adaptor may be an adaptor integrated with the drape.

In the example of the second embodiment, the sensors 320*a* (the first sensor) and the sensors 320*b* (the second sensor) are provided on one side of the detection members 213 in the direction in which the detection members 213 move (in the Z2 direction). The disclosure is not limited thereto. In the disclosure, the first and second sensors may be provided on respective sides of the detection member in the direction in which the detection member moves. In a modification illustrated in FIG. 23, for example, a sensor 420*b* is provided instead of the sensor 320*b*. FIG. 23 illustrates a state where the drape, adaptor, and surgical instrument are not attached to the robot arm 21. In this modification, the sensor 320*a* and sensor 420*b* are provided on respective sides (the Z2 side and Z1 side) of the detection member 213 in the direction in which the detection member 213 moves. The detection member 213 of the modification includes an annular detection portion 213*f*. The sensor 420*b* is configured to detect the detection member 213 when the detection portion 213*f* blocks the light in the sensor 420*b*. The sensor 420*b* is configured to be in either the light blocked state or light receiving state opposite to the sensors 320*b* of the tables illustrated in FIGS. 18 to 22 (not described in detail). To be specific, the sensor 420*b* is in the light blocked state (Low) in the state where the drape, adaptor, and surgical instrument are not mounted on the robot arm 21, in the state where the drape is positioned on the robot arm 21, and in the state where the drape and adaptor are mounted (positioned) on the robot arm 21 and the drive transmission member of the adaptor is not engaged with the driver 210, because the detection member 213 blocks the light in the sensor 420*b*. The sensor 420*b* is in the light receiving state (High) in the state where the drape and adaptor are mounted on the robot arm 21 and the drive transmission member of the adaptor is engaged with the driver, in the state where the surgical instrument is further mounted (positioned) on the robot arm 21 and the driven member of the surgical instrument is not engaged with the drive transmission member of the adaptor, and in the state where the surgical instrument is mounted on the robot arm 21 and the driven member of the surgical instrument is engaged with the drive transmission member of the adaptor, because the detection member 213 does not block the light in the sensor 420b. The sensor 420b is an example of the second sensor.

The invention claimed is:

1. A driver interface which is provided to a robot arm of a robotic surgical system and to which a housing of a surgical instrument is to be attached with an adaptor interposed between the driver interface and the surgical instrument for transmitting drive from the driver interface to the surgical instrument through a drive transmission member rotatably provided in the adaptor, the driver interface comprising:
   an engagement member which is rotatable about a rotation axis parallel to a rotation axis of the drive transmission member, wherein the engagement member includes a first engagement portion including one of an engagement protrusion and an engagement recess provided at a surface of the engagement member and provided corresponding to a second engagement portion including the other of the engagement protrusion and the engagement recess provided at the drive transmission member of the adaptor;
   an actuator which is configured to rotate the engagement member;
   a detection member comprising a contact part and movable with respect to the engagement member in a direction parallel to the rotation axis of the engagement member, the contact part configured to come in contact with a part of the drive transmission member; and
   a sensor which is configured to detect the detection member that has moved as a result of contact with the part of the drive transmission member.

2. The driver interface according to claim 1, wherein the sensor comprises a transmission-type optical sensor which detects the detection member upon light blockage by the detection member.

3. The driver interface according to claim 1, wherein the detection member is provided to be movable relative to the engagement member in the direction parallel to the rotation axis with a spring.

4. The driver interface according to claim 1, wherein the engagement member is provided such that the engagement member does not move in the direction parallel to the rotation axis and rotates about the rotation axis by the actuator.

5. The driver interface according to claim 1, wherein the sensor includes a first sensor and a second sensor configured to detect the detection member at a different moment from that of the first sensor.

6. The driver interface according to claim 5, wherein the first sensor and the second sensor detect the detection member at different positions in the direction in which the detection member moves.

7. The driver interface according to claim 6, further comprising:
   a first substrate section on which the first sensor is provided, and
   a second substrate section on which the second sensor is provided, wherein
   the first and second substrate sections are provided at different positions in the direction in which the detection member moves.

8. A driver interface provided to a robot arm of a robotic surgical system for transmitting drive to a surgical instrument through a drive transmission member rotatably provided in an adaptor, the driver interface comprising:
   an engagement member which is rotatable about a rotation axis parallel to a rotation axis of the drive transmission member, wherein the engagement member includes an engagement protrusion protruding from a surface of the engagement member and provided corresponding to an engagement recess provided at the drive transmission member of the adaptor;
   an actuator which is configured to rotate the engagement member;
   a detection member movable with respect to the engagement member in a direction parallel to the rotation axis of the engagement member; and
   a sensor which is configured to detect the detection member that has moved as a result of contact with a part of the drive transmission member, wherein
   the engagement protrusion includes a first engagement protrusion and a second engagement protrusion, and
   the detection member includes a contact section arranged between the first and second engagement protrusions and configured to come into contact with the part of the drive transmission member.

9. The driver interface according to claim 8, wherein the contact section of the detection member comprises a contact protrusion protruding from a surface of the detection member.

10. The driver interface according to claim 8, wherein the detection member is configured to be rotated together with the engagement member by the actuator, and the contact section of the detection member is positioned at a center of rotation of the engagement member and the detection member.

11. The driver interface according to claim 10, wherein the detection member includes a detection portion which is located outside the engagement member and which is to be detected by the sensor.

12. The driver interface according to claim 11, wherein the detection portion of the detection member is annular.

13. The driver interface according to claim 8, wherein the engagement member includes a guide section provided between the first and second engagement protrusions and recessed from the surface of the engagement member in an opposite direction to a direction in which the first and second engagement protrusions protrude, and
   the contact section of the detection member is provided at a position corresponding to the guide section.

14. The driver interface according to claim 13, wherein the detection member includes a guided section movably engaged with the guide section of the engagement member such that the detection member is movable with respect to the engagement member along the guide section in the direction parallel to the rotation axis.

15. A robotic surgical apparatus, comprising:
   an adaptor including a drive transmission member rotatably provided therein; and
   a robot arm which includes a driver interface to which a housing of a surgical instrument is to be attached with the adaptor interposed therebetween and which transmits drive to the surgical instrument through the drive transmission member, wherein
   the drive transmission member includes a second engagement portion,
   the driver interface includes:
   an engagement member which is rotatable about a rotation axis parallel to a rotation axis of the drive transmission member, wherein the engagement member includes a first engagement portion including one of an engagement protrusion and an engagement recess provided at a surface of the engagement member and provided corresponding to the second engagement portion including the other of the engagement protrusion and the engagement recess provided at the drive transmission member;

an actuator which is configured to rotate the engagement member;

a detection member comprising a contact part and movable with respect to the engagement member in a direction parallel to the rotation axis of the engagement member, the contact part configured to come in contact with a part of the drive transmission member; and a sensor which detects the detection member that has moved as a result of contact with the part of the drive transmission member.

16. The robotic surgical apparatus according to claim 15, wherein
the drive transmission member includes a first member including the second engagement portion and a second member movable relative to the first member with a spring,
the first member includes a pressing section and a through-hole which is formed within the second engagement portion,
the second member includes an insertion section which is to be inserted into the through-hole, and
the sensor includes a first sensor and a second sensor which is capable of detecting the detection member at a different moment from that of the first sensor, such that the first sensor detects the detection member that has moved as a result of contact with the insertion section, and the second sensor detects the detection member that has moved as a result of contact with the pressing section.

17. The robotic surgical apparatus according to claim 16, wherein
a length of the insertion section is greater than a length of the pressing section in the direction in which the detection member moves.

18. The robotic surgical apparatus according to claim 16, wherein
the pressing section and the insertion section are provided concentrically about a center of rotation of the detection member, and
the detection member includes a surface which comes into contact with both the pressing section and the insertion section.

* * * * *